(12) United States Patent
Rao

(10) Patent No.: US 11,622,943 B2
(45) Date of Patent: Apr. 11, 2023

(54) SYSTEM AND METHOD FOR ALLERGEN-SPECIFIC EPICUTANEOUS IMMUNOTHERAPY

(71) Applicant: Chamkurkishtiah Panduranga Rao, Mohawk, NY (US)

(72) Inventor: Chamkurkishtiah Panduranga Rao, Mohawk, NY (US)

( * ) Notice: Subject to any disclaimer, the term of this patent is extended or adjusted under 35 U.S.C. 154(b) by 206 days.

(21) Appl. No.: 16/869,081

(22) Filed: May 7, 2020

(65) Prior Publication Data
US 2020/0352874 A1    Nov. 12, 2020

Related U.S. Application Data

(60) Provisional application No. 62/845,947, filed on May 10, 2019.

(51) Int. Cl.
| | | |
|---|---|---|
| A61K 9/70 | (2006.01) | |
| A61K 9/00 | (2006.01) | |
| A61K 39/12 | (2006.01) | |
| A61K 39/00 | (2006.01) | |

(52) U.S. Cl.
CPC .......... *A61K 9/7084* (2013.01); *A61K 9/0014* (2013.01); *A61K 39/12* (2013.01); *A61K 2039/54* (2013.01); *A61K 2039/545* (2013.01); *A61K 2039/55583* (2013.01)

(58) Field of Classification Search
CPC .... A61K 9/7084; A61K 9/0014; A61K 39/12; A61K 2039/55583; A61K 2039/545; A61K 2039/54
See application file for complete search history.

(56) References Cited

U.S. PATENT DOCUMENTS

| | | | |
|---|---|---|---|
| 2007/0232956 A1* | 10/2007 | Harman | A61B 5/15105 600/573 |
| 2010/0330127 A1 | 12/2010 | Saito et al. | |
| 2011/0066217 A1 | 3/2011 | Diller et al. | |
| 2014/0335110 A1 | 11/2014 | Onikienko et al. | |
| 2016/0331834 A1 | 11/2016 | Mondoulet et al. | |
| 2018/0199878 A1* | 7/2018 | Smith | A61B 5/1032 |

FOREIGN PATENT DOCUMENTS

| | | | | |
|---|---|---|---|---|
| WO | WO-9829134 A2 * | 7/1998 | ............ | A61B 1/313 |
| WO | WO-2007028167 A2 * | 3/2007 | ............ | A61B 17/20 |
| WO | WO-2009008988 A1 * | 1/2009 | ............ | A61K 31/74 |
| WO | WO-2015168646 A1 * | 11/2015 | ............ | A61K 39/099 |

OTHER PUBLICATIONS

Catharine Sabatos-Peyton, Johan Verhagen, & David Wraith, Antigen-Specific Immunotherapy of Autoimmune and Allergic Diseases, 22 Curr. Opin. Immunol. 609 (Year: 2010).*

International Search Report and Written Opinion for PCT/US2020/032052; dated Sep. 24, 2020; 14 pgs.
Epicutaneous immunotherapy induces gastrointestinal LAP* regulatory T cells and prevents food-induced anaphylaxis; Tordesillas et al.; J Allergy Clin Immunol; vol. 139, No. 1; Jan. 2017; 17 pgs.
Efficacy of Epicutaneous Immunotherapy in Children with Milk-Induced Eosinophilic Esophagitis; Spergel et all; Alimentary Tract; Clinical Gastroenterology and Hepatology; vol. 18, No. 2; Feb. 2020; 16 pgs.
723 Epicutaneous immunotherapy with peanut directly targets Langerhans cells in human skin; Dioszeghy et al.; J Allergy Clin Immunol; vol. 141; No. 2; 1 pg.
P240 Skin dendritic cells progressively subvert the acti-vacation of pathogenic type-2 immunity upon epicutaneous allergen immunotherapy; Laoubi et al.; World Allergy Organization Journal; 2020; 2 pgs.
489 Efficacy of Laser Facilitated Epicutaneous Immunotherapy with Dermatophagoides pteronyssinus Depigmented Extract in a Mouse Model of Allergy; Lobo et al.; J Allergy Clin Immunol; Feb. 2020; 1 pg.
Estimated risk reduction to packaged food reactions by epicutaneous immunotherapy (EPIT) for peanut allergy; Remington et al.; Ann Allergy Asthma Immunol 123; 2019; 8 pgs.
The Clinical Utility of Epicutaneous Immunotherapy for Peanut Allergy; Samstein et al; Practice Options From Beyond Our Pages; J Allergy Clin Immunol Pract; Sep. Oct. 2019; 2 pgs.
Specific epicutaneous immunotherapy prevents sensitization to new allergens in a murine model; Mondoulet et al.; J Allergy Clin Immunol; vol. 135, No. 6; Jun. 2015; 16 pgs.
Peanut-allergic experiences after epicutaneous immunotherapy: peanut consumption and impact on QoL; Lewis et al.; Ann Allergy Asthma Immunol 123; 2019; 3 pgs.
Epicutaneous immunotherapy for peanut allergy modifies IgG$_4$ responses to major peanut allergens; Koppelman et al.; J Allergy Clin Immunol; vol. 143; No. 3; Mar. 2019; 8 pgs.
Delivery of allergen powder for safe and effective epicutaneous immunotherapy; Yu et al.; Biologies and immunotherapy; J Allergy Clin Immunol; vol. 145; No. 2; Feb. 2020; 13 pages.
Significantly increased threshold does after long-term peanut epicutaneous immunotherapy and daily oral peanut intake; Fink et al.; Ann Allergy Asthma Immunol 124; 2020; 4 pgs.
Epicutaneous immunotherapy; Scheurer et al.; Allergol Immunopathol (Madr); 45(S1); 2017; 5 pgs.

(Continued)

*Primary Examiner* — Sean M Basquill
(74) *Attorney, Agent, or Firm* — Barclay Damon LLP

(57) ABSTRACT

A method of immunological evaluation includes cleaning a skin surface area of a patient. A controlled amount of heat is then applied to the skin surface area. The controlled amount of heat is removed after the skin surface area reaches a predetermined temperature. An amount of antigen is deposited onto the skin surface area and incubated for a predetermined amount of time on the skin surface area. The antigen is removed from the skin surface area and an immunological response at the skin surface area is evaluated. Apparatus for administering heat and memorializing the evaluation are also disclosed.

13 Claims, 22 Drawing Sheets

(56) References Cited

OTHER PUBLICATIONS

The regulatory T cells induction by epicutaneous immunotherapy is sustained and mediates long-term protection from eosinophilic disorders in peanut-sensitized mice; V. Dioszeghy et al.; Clinical & Experimental Allergy; pp. 867-881; © 2014; 15 pgs.

Epicutaneous Immunotherapy (EPIT) Blocks the Allergic Esophago-Gastro-Enteropathy Induced by Sustained Oral Exposure to Peanuts in Sensitized Mice; L. Mondoulet et al.; www.plosone.org; vol. 7; Issue 2; © Feb. 2012; 10 pgs.

Epicutaneous immunnotherapy in rhino-conjunctivitis and food allergies: a review of the literature; S. Esposito et al.; Journtal of Translational Medicine; © 2018; 8 pgs.

Transdermal patches: history, development and pharmacology; M. Pastore et al.; British Journal of Pharmacology; www.briplharmacol.org; pp. 2179-2209; © 2015; 31 pgs.

Transcutaneous antigen delivery system; M. Lee et al.; The Korean Society for Biochemistry and Molecular Biology; http://bmbreports.org; pp. 17-24; © 2013; 8 pgs.

Flexible Delivery Patch Systems based on Thermoresponsive Hydrogels and Submicronic Fiber Heaters; A. Evanghelidis et al.; Scientific Reports; www.nature.com/scientificreports; © 2018; 10 pgs.

Dermal Patch with Integrated Flexible Heater for on Demand Drug Delivery; S. Bagherifard et al.; Advanced Healthcare Materials; www.advhealthmat.de; © 2015; 1 pg.

International Preliminary Report on Patentability for PCT/US2020/032052; dated Nov. 16, 2021; 11 pgs.

Novel mechanisms in immune tolerance to allergens during natural allergen exposure and allergen-specific immunotherapy; van de Veen et al.; www.sciencedirect.com; Current Opinion in Immunology 2017, 48: 74-81.

Differences in phenotype, homing properties and suppressive activities of regulatory T cells induced by epicutaneous, oral or sublingual immunotherapy in mice sensitized to peanut; Dioszeghy et al.; Cellular & Molecular Immunology (2017) 14, 770-782; www.nature.com/cmi.

Epicutaneous immunotherapy induces gastrointestinal LAP+ Tregs and prevents food-induced anaphylaxis; Tordesillas, PhD et al.; Author manuscript; J Allergy Clin Immunol. Jan. 2017.

Intact skin and not stripped skin is crucial for the safety and efficacy of peanut epicutaneous immunotherapy (EPIT) in mice; Mondoulet et al.; Clinical and Translational Allergy 2012; http://www.ctajournal.com/content/2/1/22; 12 pages.

Is epicutaneous immunotherapy only skin deep? Katz, MD et al.; J. Allergy Clin Immunol; Apr. 2017; 2 pages.

* cited by examiner

SYSTEM AND METHOD FOR ALLERGEN-SPECIFIC EPICUTANEOUS IMMUNOTHERAPY

CROSS REFERENCE TO RELATED APPLICATION

Pursuant to relevant sections of 35 U.S.C. § 119 and 37 CFR § 1.53, this application claims the benefit and priority of U.S. Patent Application No. 62/854,947, filed on May 10, 2019, the entire contents of which is hereby incorporated by reference.

TECHNICAL FIELD

This application is directed generally to the field of immunology and more specifically to a novel system and method for allergen-specific epicutaneous immunotherapy using a device that locally heats a skin surface of a patient prior to the application of a controlled amount of an antigen to the heated skin surface.

BACKGROUND

Allergen-specific immunotherapy is a common form of treatment whose primary aim is to desensitize patients with severe allergies. This form of therapy often may require periodic treatments of a patient extending over a prolonged period of time, typically using a series of injections. These treatments may result in a reduction or completely eliminate the patient's allergic response to a specific allergen. This therapy is done by generating allergen-tolerant T-cells over time, which is manifested in a decrease in specific-IgE antibody levels and an increase in specific-IgG antibody levels, or an increase in the ratio of specific-IgG/IgE antibodies.

Another form of allergen-specific immunotherapy that has been shown to be safe and efficacious in the treatment of allergies in humans is epicutaneous immunotherapy (EPIT). Epicutaneous immunotherapy allows for an antigen uptake to occur across the skin, rather than subjecting the patient to injections. Similarly, specific-IgE and specific-IgG antibody levels are measured and a decrease in specific-IgE antibodies or more specifically, an increase in the specific-IgG/IgE antibody ratio is indicative of the generation of allergen-tolerant T-cells.

Epicutaneous immunotherapy is usually accomplished using a transdermal patch that adheres to the skin and is worn for a predetermined period of time. One known type of transdermal patch has a dried form of the desired antigen, which is held between two spaced membranes. The membrane that is closest to the surface of the skin is semipermeable and allows moisture evaporated from the skin to pass and solubilize the dried antigen. The solubilized antigen then passes through the membrane and onto the surface of the skin via the patch, which is adhered to the skin surface. The solubilized antigen does not readily absorb or pass though the intact skin surface and instead is taken up by Langerhans cells, which in turn present the antigen to T-cells in the regional lymph node. It has been determined that transdermal patches must be worn for several days to produce desired effects. In addition, it has been found that this form of therapy has proven to be effective only in young patients (i.e., those patients under 13 years old).

Other forms of epicutaneous immunotherapy are known in the field, each involving some form of disruption of the epidermis. An epicutaneous based method for the determination of various diseases is lacking. For example, tuberculosis (TB) is a worldwide infectious disease and more specifically the top infectious killer in the world. There were a reported total of 10.4 million new cases of TB, including 1 million cases of TB in children in 2016. According to the 2017 World Health Organization's (WHO's) Global Tuberculosis Report, 1.7 million people died of TB in 2016. While TB is quite rare in countries such as the United States, TB is still very prevalent in the underdeveloped world, in which approximately ⅓ of the world population has been exposed to this disease and wherein the majority of cases are in the latent or dormant phase. It is presumed that reactivation of latent TB is a predominant cause of the spread of this disease.

From a clinical point of view, physicians would like to diagnose and treat TB as soon as possible in order to present the spread of the disease. Presently, the so-called Mantoux test is the gold standard for purposes of the identification of exposure to TB as endorsed by the Centers for Disease Control and Prevention (CDC). The Mantoux test (also referred to as the "Mendel-Mantoux test") involves an intradermal injection of a small amount (0.1 ml) of PPD (purified protein derivative) tuberculin as a screen for TB usually in the forearm of the patient. The results from the Mantoux test are based on the reaction as the person who is exposed to the bacteria will mount an immune response at the injection site. The level (diameter) of induration is indicative of the result of this screen. However, this test is based on the delayed hypersensitivity principle, in which the forearm site must be read by a professional 48-72 hours after the injection for determination of a reaction. This delayed time frame is not very efficacious and therefore it would be very beneficial to have a test that is based on innate immunity memory, which renders reliable results in a matter of hours instead of 2-3 days.

The foregoing background describes some, but not necessarily all problems, disadvantages and shortcomings related to current epicutaneous allergen-specific immunotherapy. There is a general and pervasive need in the field to provide an epicutaneous (EPIT) allergen-specific immunotherapy technique that is reliable, easy and inexpensive to administer, and effective in patients of all ages.

SUMMARY

The current disclosure is directed to a tissue or skin heating device and a method of immunotherapy, immunization, and determining innate immunity using an epicutaneous treatment. In an embodiment, a method of immunological evaluation comprises cleaning a skin surface area of a patient and applying a controlled amount of heat to the skin surface area. The controlled amount of heat is removed after the skin surface area reaches a predetermined temperature. An amount of an antigen is administered onto to the skin surface area and incubated for a predetermined amount of time on the skin surface area. The antigen is removed from the skin surface area and an immunological response at the skin surface area is evaluated.

In an embodiment, a method of performing a booster immunization relative to a patient comprises cleaning a skin surface area of the patient and heating the skin surface area to a predetermined temperature. A prescribed amount of a vaccine is applied to the skin surface area and incubated for a predetermined amount of time. The prescribed amount of the vaccine is then removed from the skin surface area.

In an embodiment, a system for performing immunotherapy on a patient comprises a skin heating device. The skin heating device comprises a source of heat and at least one contact surface coupled to the source of heat and being adapted to contact a skin surface area. The skin heating device further comprises a temperature sensor electrically coupled to the at least one contact surface, a display coupled to the temperature sensor and configured to display a temperature reading of the at least one contact surface, and a processor configured to automatically turn off the source of heat when the predetermined temperature is reached at the at least one contact surface. An antigen delivery device is configured to deliver a dose of an antigen to the skin surface area and a monitoring apparatus is configured to support a smart device for capturing at least one image of the skin surface area of the patient after the delivery of the dose of antigen thereto.

An embodiment of a skin heating device for immunotherapy treatment of a patient comprises a heat applicator. The heat applicator comprises a source of heat, at least one contact surface coupled to the source of heat and being configured to a skin surface area of a patient, and a temperature sensor electrically coupled to the at least one contact surface. A display is coupled to the temperature sensor and configured to display a temperature reading of the at least one contact surface. A processor is configured to automatically turn off the source of heat after a predetermined temperature is sensed by the temperature sensor. The skin surface area is conducive for immunotherapy treatment following heating to the predetermined temperature.

An embodiment of an antigen cap comprises a base portion and a top portion. The base portion comprises one or more sides defining a perimeter and having a contact end configured to be placed in contact with a skin surface area of a patient. A holder is positioned within the perimeter of the base portion and configured to retain an antigen capsule containing a dose of antigen. One or more spikes are positioned at least partially within the holder. The top portion is configured to move relative to the base portion between an open position and a closed position that covers the holder of the base portion. In the closed position, the one or more spikes are configured to engage and pierce the retained antigen capsule to expel the dose of antigen.

BRIEF DESCRIPTION OF THE DRAWINGS

Some of the embodiments will be described in detail, with reference to the following figures, wherein like designations denote like members.

DEFINITIONS

For purposes of the following description, the following terms are herein defined as follows:

An "allergen" is a type of antigen that produces an abnormally vigorous immune response.

An "antigen" is a toxin or other foreign substance that induces the production of antibodies.

Immunoglobulin E (IgE) is a mammalian antibody which plays an essential role in type 1 hypersensitivity, which manifests in various allergic diseases, such as allergic asthma, most types of sinusitis, allergic rhinitis, food allergies, and specific types of chronic urticaria and atopic dermatitis. IgE also plays a pivotal role in responses to allergens, such as anaphylactic drugs, bee stings, and antigen preparations used in desensitization immunotherapy.

Immunoglobulin G (IgG) is the most common type of antibody found in the blood and extracellular fluid and plays a key role in controlling infection. Clinically, measured IgG antibody levels are generally considered to be indicative of an individual's immune status to particular pathogens.

Immunoglobulin G4 (IgG4) is a subclass of IgG antibodies that appear only after prolonged immunization. In the context of IgE-mediated allergy, the appearance of IgG4 antibodies is usually associated with a decrease in symptoms.

Interferon γ is a cytokine that is critical for innate and adaptive immunity against viral, bacterial, and protozoal infections. Interferon γ is an important activator of macrophages and inducer of Class II major histocompatibility complex (MEW) molecule expression.

DETAILED DESCRIPTION

The following discussion relates to various embodiments of a system and method of allergen-specific epicutaneous immunotherapy. It will be understood that the herein described versions are examples that embody certain inventive concepts. To that end, other variations and modifications will be readily apparent to those of sufficient skill in the field. In addition, a number of terms are used throughout this discussion in order to provide a suitable frame of reference with regard to the accompanying drawings. These terms such as "forward", "rearward", "interior", "exterior", "front", "back" and the like are not intended to limit these concepts, except where so specifically indicated. In addition, the drawings are intended to depict salient features of the inventive device for use in the system and method of allergen-specific epicutaneous immunotherapy. Accordingly, the drawings are not specifically provided to scale and should not be relied upon for scaling purposes.

Figure 1A:
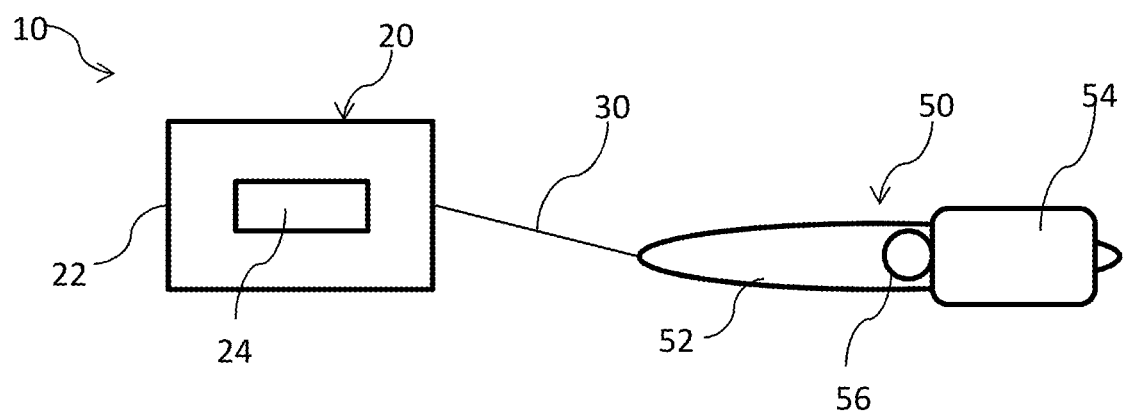
FIG. 1(a) illustrates a schematic view of an embodiment of a tissue heating device with an embodiment of a probe of the device shown from a bottom side.
Figure 1B:
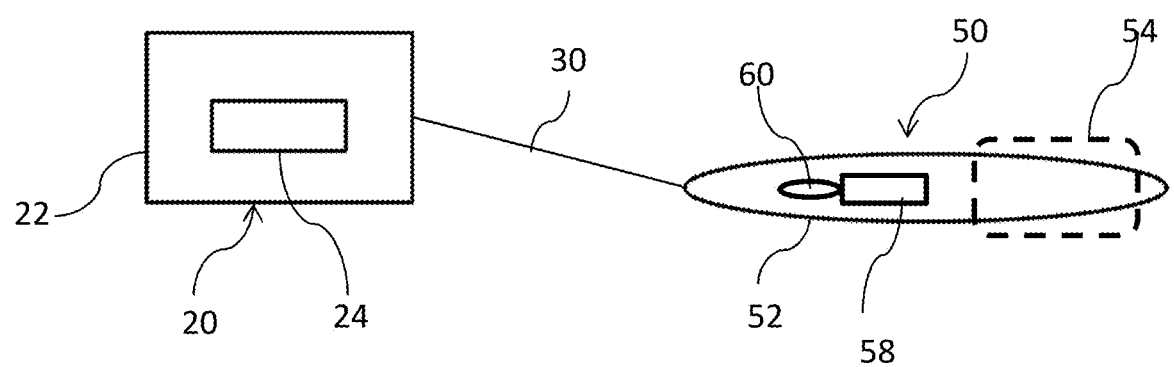
FIG. 1(b) illustrates a schematic view of an embodiment of the tissue heating device of FIG. 1(a) with an embodiment of the probe shown from the top side.
Figure 2:
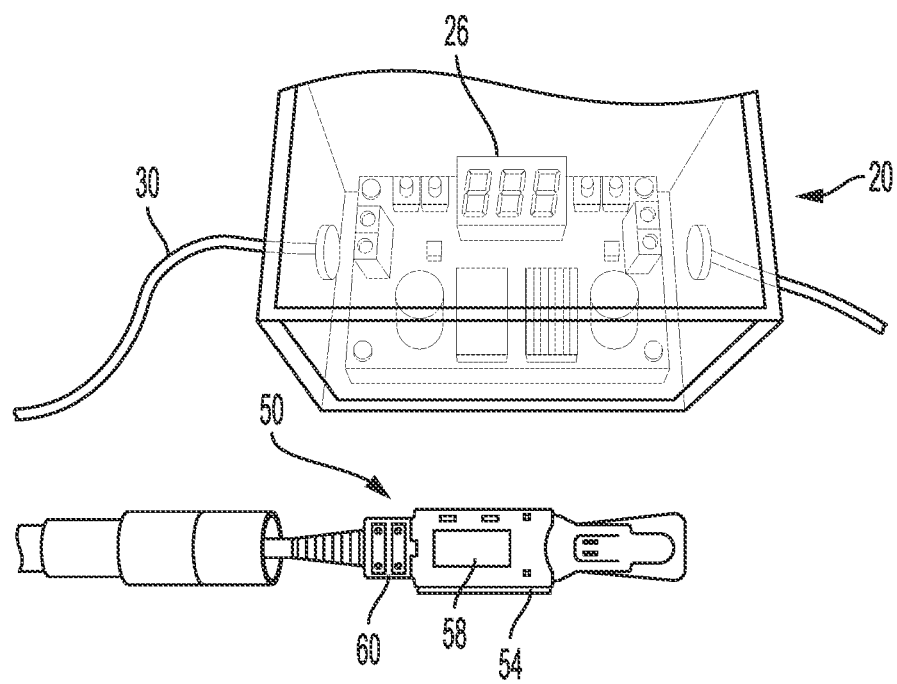
FIG. 2 illustrates another embodiment of a tissue heating device made in accordance with aspects of the invention.

Referring to FIGS. 1(a) and 1(b), a skin surface (also synonymously referred to as a "tissue") heating device 10 made in accordance with a first embodiment comprises a housing 20 and a probe 50 that is electrically coupled to the housing 20. In the herein illustrated embodiment, the probe 50 is mechanically and electrically coupled to the housing 20 by an electrical cord 30, although the probe 50 could alternatively be in communication with one or more components within the housing 20 using a wireless form of connection such as but not limited to RF, IR or Bluetooth. The housing 20 is defined by an enclosure 22 having an interior that is sized, shaped and configured to retain a plurality of components, including a control unit 24. The housing 20 can be comprised of any suitable material to be used in a medical setting, such as, for example, a durable, non-reactive plastic. In an embodiment, the contained control unit 24 may further be coupled to a user interface that includes at least one or more adjustment elements in the form of buttons, switches, and/or knobs that are preferably positioned on an exterior surface of the housing 20 such that the adjustment elements can be accessed and manipulated by a user. Alternatively, the contained control unit 24 may be coupled to an external display 26 (FIG. 2) that presents information regarding operation to the user.

The housing 20 is preferably portable in which the interior also contains one or more batteries (not shown) disposed in a compartment (not shown) that provide electrical power to the tethered probe 50. The one or more batteries (not shown) can be any suitable kind of rechargeable batteries that allow for long periods of operation between charging. Preferably, the housing 20 can include a cover (not shown) to permit removal of the batteries from the interior compartment for replacement or recharging. In another version, the housing 20 can include one or more charging ports (not shown) that extend outwardly from the housing 20. In this latter version, the housing 20 is suitably shaped and configured to be positioned within a charging cradle or charging station (not shown). In yet another version, the housing 20 can be suitably configured to enable connection to an external AC power supply (not shown) to permit the contained batteries to be charged or the housing 20 can be configured for direct connection to the external AC power supply, which can provide electrical power to the tethered probe 50.

Referring to FIGS. 1(a) and 1(b) and according to this specific embodiment, the probe 50 is defined by a generally elongate probe body 52 having an interior that supports or retains a plurality of components. According to one embodiment, the probe body 52 may be made from the same or similar material as the housing 20 or can be fabricated from another suitable structural and durable material. Referring to FIG. 1(a), the bottom side of the probe 50 includes a substantially planar contact surface 54 at a proximal end of the probe body 52. As discussed herein, the contact surface 54 is sized and shaped to engage and cover a portion of a subject's skin surface and is further configured to generate heat. The contact surface 54 may itself be a heating element or alternatively may be comprised of a heat conductive material that can be heated by a heating element (not shown) that is connected to the contact surface 54. A temperature sensor 56, such as a thermistor or a thermocouple, is coupled to the contact surface 54 and configured to generate signals based on a sensed temperature of the contact surface 54. According to this embodiment, the temperature sensor 56 transmits signals to a controller 60 disposed within the probe body 52.

Figure 3A:
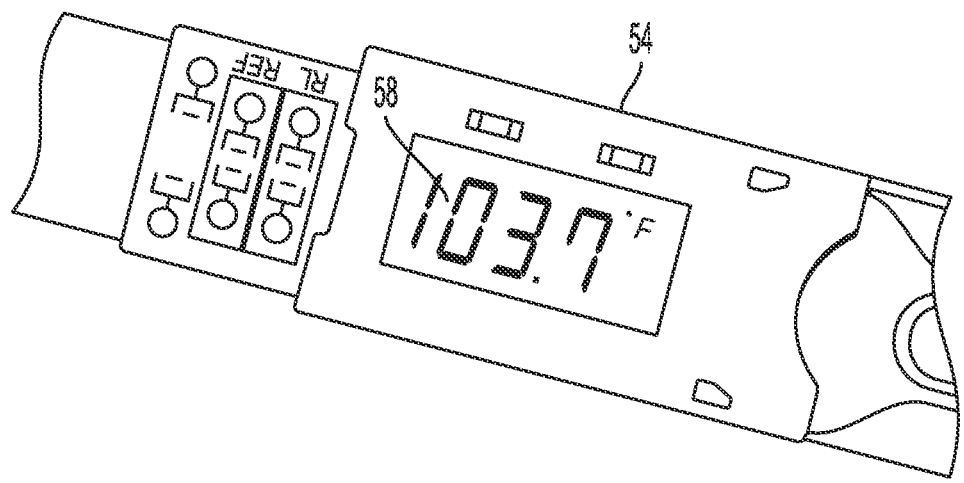
FIG. 3(a) illustrates a close up view of an embodiment of a display of a tissue heating device.
Figure 3B:
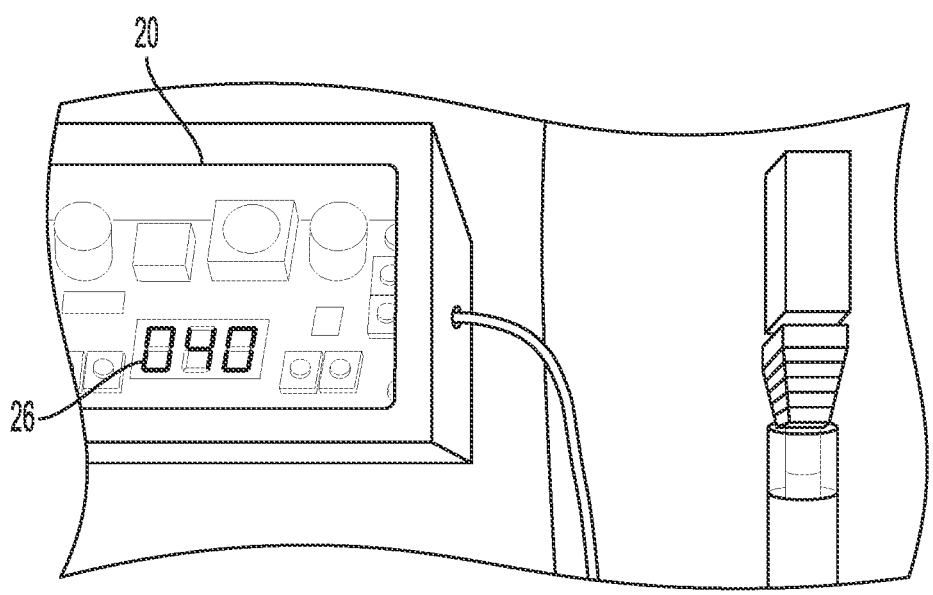
FIG. 3(b) illustrates an embodiment of a controller of a tissue heating device.

As shown in FIG. 1(b), as well as FIGS. 3(a) and 3(b), the temperature of the contact surface 54 may be presented in real time on a display 58 coupled to the controller 60 and provided on the probe body 52. Alternatively, the temperature reading can be provided on the external display 26, FIG. 2, of the tethered portable housing 20. In this regard, it will be understood that any of the various functions of the probe 50; such as, for example, displaying the temperature reading of the contact surface 54 can be provided by the housing 20. It should also be understood that the probe 50 can include all or some of the features of the housing 20. For example, the probe 50 can include an embedded power source or be directly coupled to an external AC power supply in lieu of the housing 20.

According to at least one embodiment, the controller 60 of the probe 50 may also be programmed to automatically turn off the contact surface 54 (or heating element) after a predetermined amount of time has elapsed, or more preferably after a predetermined target temperature of the contact surface 54 has been reached, as measured by the temperature sensor 56. In an embodiment, the controller 60 may be coupled to a user interface provided on the exterior surface of the probe body 52, the user interface comprising one or more buttons, switches, knobs or other adjustment elements to enable manual control during immunotherapy treatments, as discussed herein. These control functions may also be provided as part of a touchscreen of the external display.

In operation, the herein described skin surface heating device 10 is intended to generate heat for purposes of heating a skin site of a patient to a predetermined temperature for purposes of immunotherapy treatments. The contact surface 54 of the probe 50 is placed in contact with the skin surface of a patient and the heating source is energized. When the predetermined temperature is reached, the heating source is deenergized automatically. Details relating to a method of using the heating device and immunotherapy using the heating device are discussed in a later section of this description.

Another embodiment of the skin surface heating device 100 is illustrated in FIGS. 3(c)-(f). The skin surface heating device 100 generally comprises a housing 120 coupled to a skin contact element or skin contact portion 150 that is electrically coupled to the housing 120. In the herein illustrated embodiment, the skin contact element 150 is mechanically and electrically coupled to the housing 120 by an electrical cord 130, although the skin contact element 150 could alternatively be in communication with one or more components within the housing 120 using a wireless form of connection such as but not limited to RF, IR or Bluetooth. As shown, the housing 120 is defined by an enclosure 122 having an interior that is sized, shaped and configured to retain a plurality of components, including a control unit 24 (FIG. 1). The housing 120 may be comprised of any suitable material to be used in a medical setting, such as, for example, a durable, non-reactive plastic. In an embodiment, the contained control unit 24 (FIG. 1) may further be coupled to a user interface 128 that includes at least one or more adjustment elements in the form of buttons 127, switches, and/or knobs that are preferably positioned on an exterior surface of the housing 120 such that the adjustment elements can be accessed and manipulated by a user. Alternatively, the contained control unit 24 (FIG. 1) may be coupled to an external display 126 that presents information regarding operation to the user.

The housing 120 is preferably portable in which the interior also contains one or more batteries (not shown) disposed in a compartment (not shown) that provide electrical power to the skin contact element 150. The one or more batteries (not shown) can be any suitable kind of rechargeable batteries that allow for long periods of operation between charging. The housing 120 may include a cover (not shown) to permit removal of the batteries from the interior compartment for replacement or recharging. In another embodiment, the housing 120 may include one or more charging ports (not shown) that extend outwardly from the housing 120, and the housing 120 itself may be suitably shaped and configured to be positioned within a charging cradle or charging station (not shown). In another embodiment, the housing 120 may be suitably configured to enable connection to an external AC power supply (not shown) to permit the contained batteries to be charged or the housing 120 can be configured for direct connection to the external AC power supply, which can provide electrical power to the skin contact portion 120.

Figure 3C:
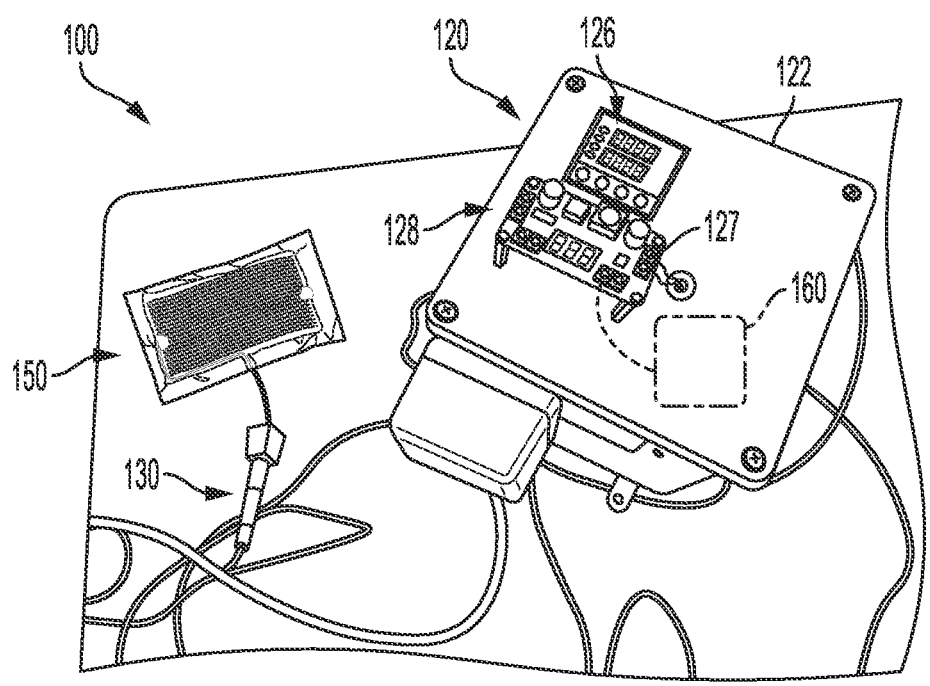
FIG. 3(c) illustrates another embodiment of a tissue heating device made in accordance with aspects of the invention.
Figure 3D:
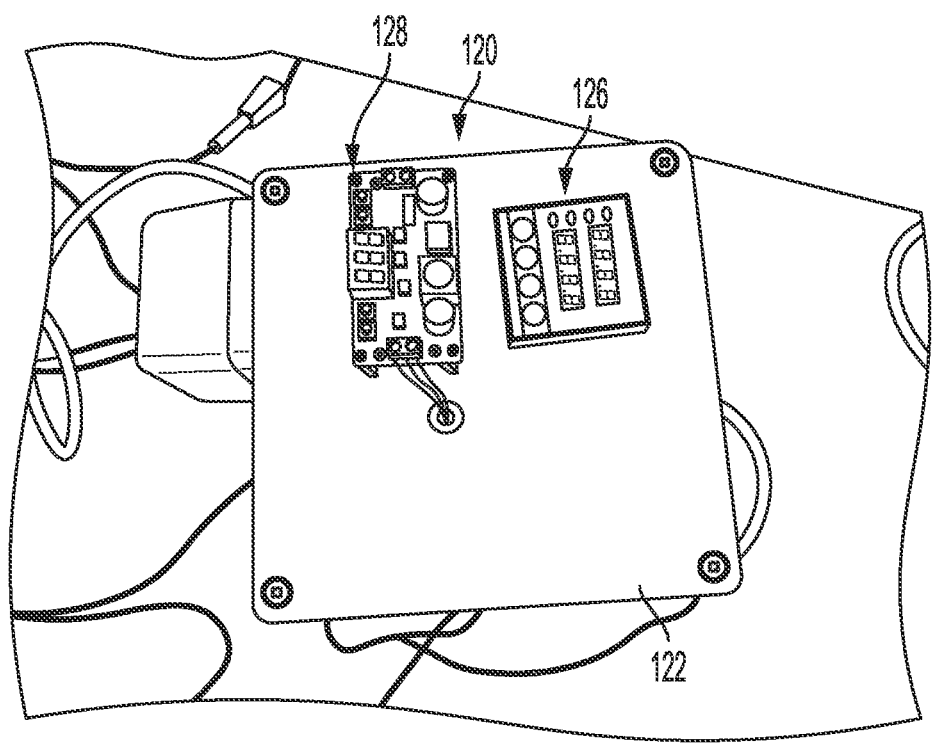
FIG. 3(d) illustrates a close up view of an embodiment of a display of the tissue heating device of FIG. 3(c)
Figure 3E:
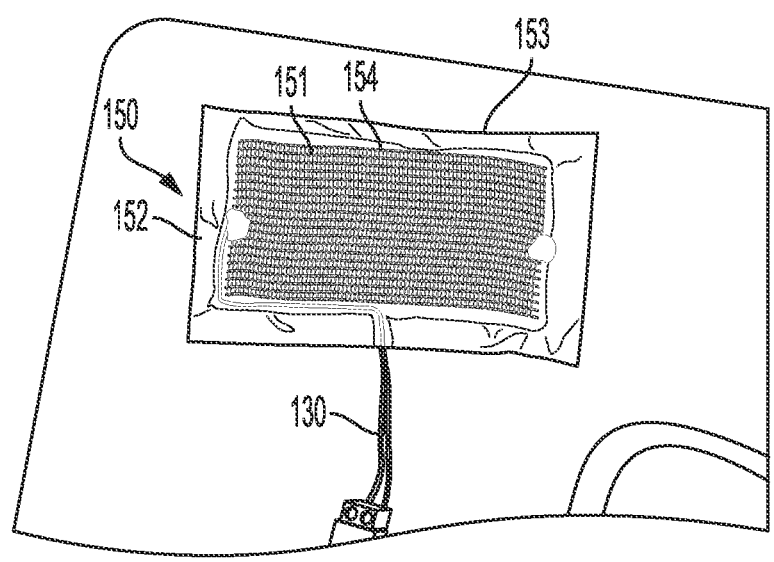
FIG. 3(e) illustrates a close up view of an embodiment of a skin contact portion of the tissue device of FIG. 3(c)
Figure 3F:
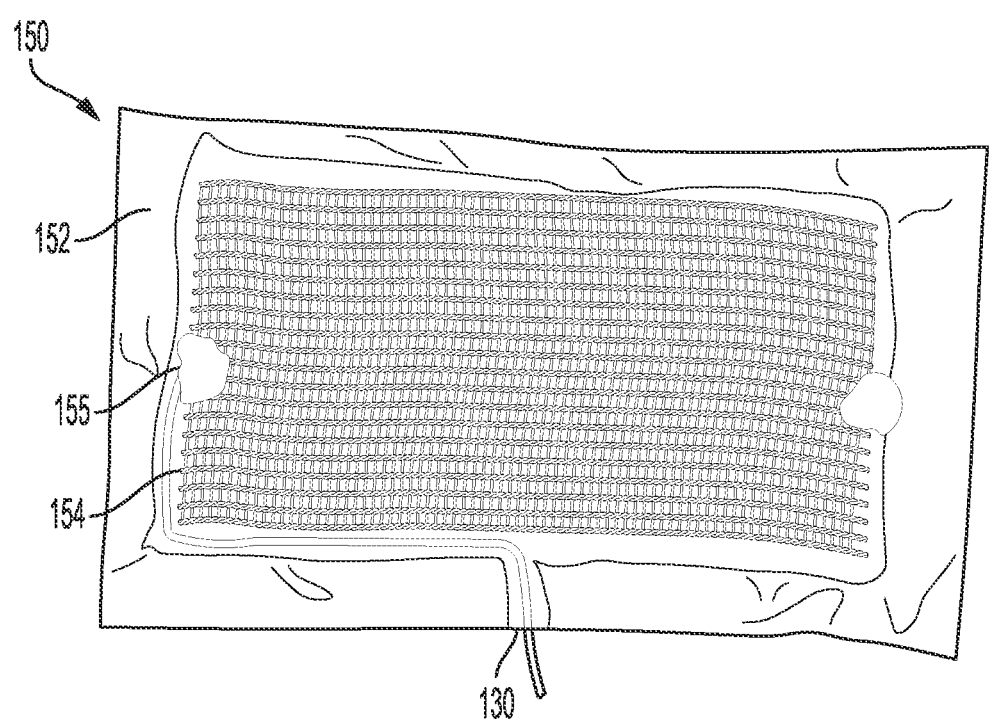
FIG. 3(f) illustrates another close up view of an embodiment of the skin contact portion of the tissue device of FIG. 3(e)

Referring to the embodiment illustrated in FIGS. 3(c), and 3(e)-3(f), the skin contact portion 150 is flexible and is defined by a planar substrate 152. The substrate 152 comprises a top side 151 and an opposing bottom or contact surface 153 (FIG. 3(e)). When the skin contact portion 150 is placed on the skin surface, the top side 151 of the substrate 152 faces away from the skin and the bottom side 153 faces and/or contacts the skin surface. As shown, a plurality of heating elements form a heating matrix 154 that is supported by the substrate 152. Each of the plurality of heating elements may be configured to heat up and/or reach a desired temperature at substantially the same time. In an embodiment, the heating matrix 154 is surrounded by the substrate 152. The heating matrix 154 is electrically coupled to one or more components within the housing 120, such as a power source by an electrical cord 130 that couples to the heating matrix 154 at a junction 155. The skin contact portion 150 may comprise additional layers depending on the specific application. For example, additional layers may be added to improve heat transfer, prevent burns, and/or release an antigen.

In another embodiment, one or more tubes may be in fluid communication with a liquid reservoir that is in contact with one or more heating elements. The one or more heating elements can transfer heat energy to the liquid in the reservoir, thereby raising the liquid temperature. The heated liquid can then be circulated (e.g., by gravity or by a pump) through the one or more tubes. The one or more tubes may be in contact with the skin surface or may be in contact with a transfer element, which in turn is in contact with the skin surface. Heat energy is therefore transferred from the heated liquid in the one or more tubes to the skin surface in order to heat the skin surface.

Figure 3G:
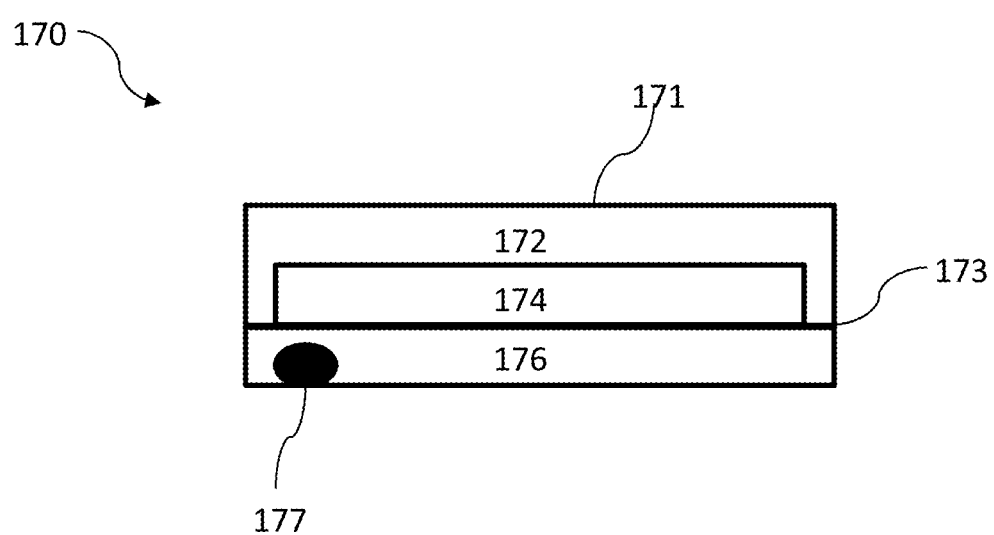
FIG. 3(g) illustrates a schematic view of another embodiment of the skin contact portion of a tissue device.

Referring specifically to FIG. 3(g), another embodiment of the skin contact portion 170 comprises a substrate layer 172 supporting a plurality of heating elements or heating matrix 174. A hydrogel layer or coating 176, such as thermoresponsive poly(N-isopropylacrilamide) (PNIPAM), is positioned in contact with the heating matrix 174 and is also supported by the substrate layer 172. The substrate 172 has a top surface 171 and bottom surface 173. Similar to other embodiments, when the skin contact portion 170 is placed onto the skin surface, the top surface 171 faces away from the skin surface and the bottom surface 173 faces towards the skin surface. In an embodiment, a metallic layer may be positioned to separate the heating matrix 174 from the hydrogel layer or coating 176. The metallic layer may be comprised of any conductive metal that is capable of efficient and consistent heat transfer. For example, the metallic layer may be comprised of aluminum. The hydrogel layer or coating 176 may contain one or more antigens of interest whose release from the hydrogel layer or coating 176 is temperature dependent. Accordingly, heating the hydrogel layer or coating 176 and, therefore the skin surface, to the desired temperature (103-105° F.) results in the release of the dosage of antigen from the hydrogel layer or coating 176. In this manner, the temperature of the skin surface may be maintained at the desired temperature during the incubation period of the antigen. The skin contact portion 170 further includes a temperature sensor 177, such as a thermistor or a thermocouple that is configured to generate signals based on a sensed temperature of the substrate 172, heating matrix 174, hydrogel layer 176, the skin surface, or any combination thereof. According to this embodiment, the temperature sensor 177 transmits signals to a controller 160 (FIG. 3(c)), shown in phantom disposed within the housing 120.

As shown in FIGS. 3(c)-(d), the temperature may be presented in real time on the display 126 coupled to the controller 160. Alternatively, the temperature reading can be provided on a display 126 coupled to the substrate 172. In an embodiment, the skin contact portion 170 may be part of the probe 50 and have similar capabilities as those discussed above.

In operation, the herein described skin surface heating device 10, 100 is intended to generate heat for purposes of heating a skin site of a patient to a predetermined temperature for purposes of immunotherapy treatments. The contact surface 54 or skin contact portion 150 is placed in contact with the skin surface of a patient and the heating source is energized. When the predetermined temperature is reached, the heating source is deenergized automatically. Details relating to a method of using the heating device and immunotherapy using the heating device are discussed in a later section of this description.

Figure 4A:
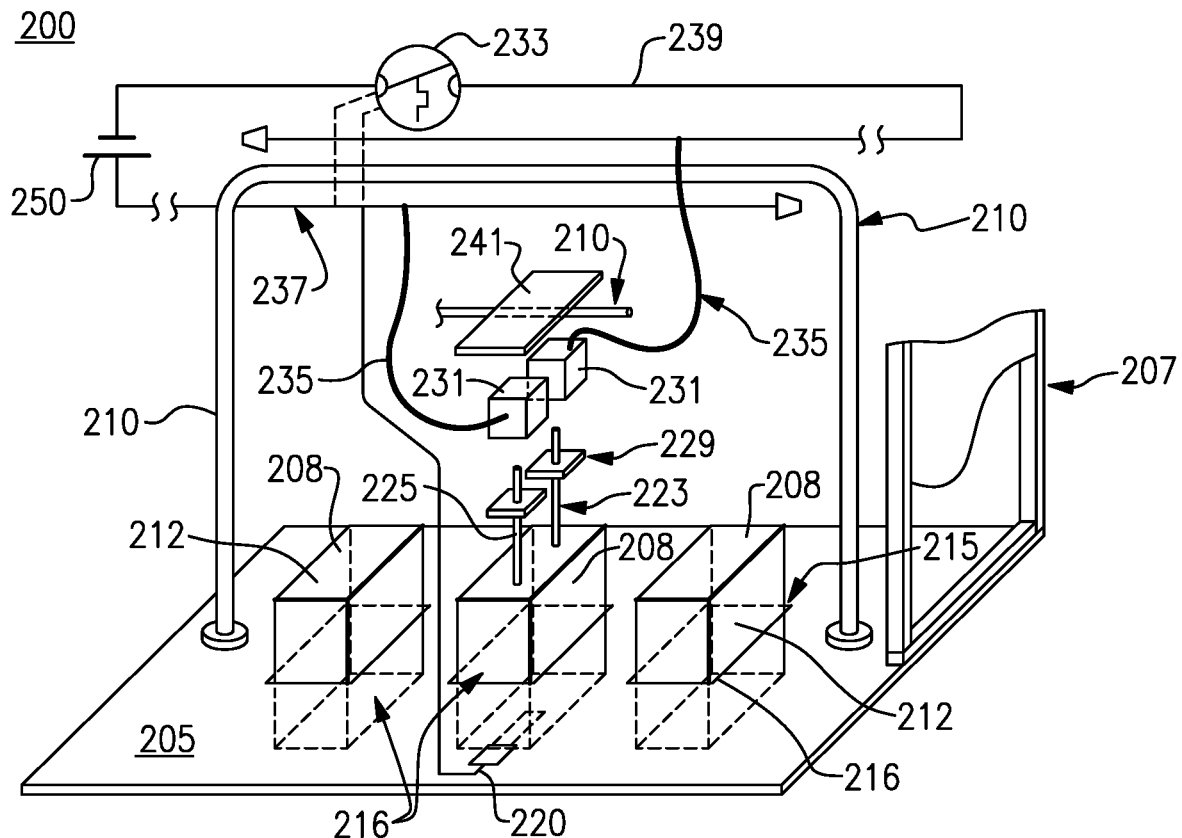
FIG. 4(a) is a partial sectioned and schematic view of a tissue heating device made in accordance with another exemplary embodiment that is effective to simultaneously heat a plurality of adjacent patient sites at the same time.

With reference to FIG. 4(a), a skin surface heating device 200 made in accordance with another embodiment is described. According to this version, a plurality of heating elements 208 are disposed within the interior of a device housing 204 in side by side adjacent relation for the purposes of contacting a plurality of skin sites on a patient (not shown). According to this version, three (3) heating elements 208 are provided, but it will be readily apparent that this parameter can be suitably varied (i.e., between one and n heating elements 208). The housing 204 according to this embodiment is defined by a horizontal base 205 made from wood, plastic or other suitable structural material and an external enclosure 207, shown only partially in this view that is connected to the horizontal base 205. In addition, a support 210 made from plastic, metal or other suitable material is fastened to the horizontal base 205 to provide structural integrity. Alternatively, the housing can be fabricated from a single component.

Each of the heating elements 208 according to this embodiment is commonly defined by an element body 212 that retains a heating element (not shown) configured for heating a skin contact surface 216 provided at one end of the element body 212, the latter surface 216 being configured to project externally from the housing 204 through a slot 215 formed in the horizontal base 205 of the device housing 204. The heating element according to at least one version can be a resistive coil that is disposed within a ceramic enclosure.

With continued reference to FIG. 4(a), the specific arrangement of a single heating element 208 is herein described for the sake of clarity. Each of the heating elements 208 further include a temperature sensor 220, such as a thermocouple or thermistor, disposed in relation to the skin contact surface 216 and coupled by an extending wire to a thermostat relay 223. According to this described version, each of the heating elements 208 further include respective input and output terminals 225, 227 that extend outwardly from the element body 212. An insulation washer 229 is provided with a center opening sized to allow individual washers 229 to be slid onto the input and output terminals 225, 227. Respective headers 231 are disposed onto the input and output terminals 225, 227, each of the headers 231 including an extending wire 235 that electrically couples the input and output terminals 225, 227 via connectors, such as T-tap connectors to electrical lines 237, 239, respectively. These electrical lines 237, 239 are electrically coupled to a power supply, such as an AC power supply shown schematically as 250, the latter being further connected to an AC/DC converter (not shown) and a voltage regulator (not shown) with the electrical line 237 being an insulated low voltage wire for DC current in and the electrical line 239 being an insulated low voltage wire for DC current out. According to this embodiment, an insulating piece 241 is attached to the metal or plastic support 210 in order to isolate the support 210 from the headers 231. The external enclosure 207 includes openings sized to allow the electrical lines 237, 239, as well as the wire of the thermostat relay 233 to pass through.

The thermostat relay 223 according to this embodiment is connected to the electrical line 239. In operation, the thermostat relay 223 is tripped automatically to electrically decouple the power supply, shown schematically as 250 in FIG. 4(b), from the electrical wire 239 once a predetermined temperature has been reached at the skin contact surface 216 of each heating element 208.

In an alternative version, a set of rechargeable batteries (not shown) can be used as a power supply, in which the batteries can be disposed within the interior of the housing 204.

Figure 4B:
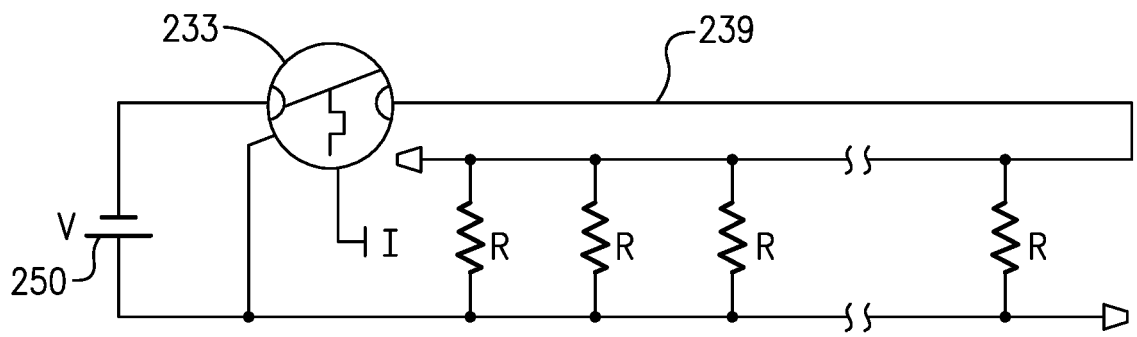
FIG. 4(b) represents a circuit diagram of the tissue heating device of FIG. 4(a)

With reference to FIGS. 4(a) and 4(b), the heating device 200 according to this described embodiment is configured and programmed to simultaneously and uniformly heat each skin contact surface 216 of each of the adjacently supported heating elements 208 (1-n) to the predetermined temperature (e.g., 103° F.-105° F.). The contact surface 216 is brought onto the skin surface of the patient (not shown). The power supply 250 is configured as shown in FIG. 4(b) to simultaneous heat each skin site in order to uniformly direct generated heat. In order to provide simultaneous or contemporaneous heating and according to this embodiment, each of the heating elements 208 of the heating device 200 are connected to the electrical line 239, the latter having equal line segments 244 attached to heat the adjacent heating elements 208 that are arranged relative to one another in parallel with the power of each resistor (heating element) being $V^2/R$, as expressed in watts with V equal to voltage, as expressed in volts and R referring to the resistance, as expressed in ohms for the number of heating elements (1 through n). It will be understood that other suitable electrical and mechanical connectors can be employed to retain each of the heating elements 208 within the device housing 204.

In accordance with the present invention and using either of the herein described skin surface heating devices 100, 200 or equivalents thereof, immunotherapy methods that can be utilized in conjunction with a varied number of applications or uses are now described in greater detail.

Thermal Epicutaneous Induction/Testing(Tei) Method

As previously noted, the standard method of determining/screening whether a patient has tuberculosis (TB) is the Mantoux test. This test is performed by a physician (or other medical professional) injecting a liquid containing an amount of PPD tuberculin under the top dermis (epidermal) layers of the patient's forearm. After an extended period of 48-72 hours, the patient must return to the physician's office to have the physician or other medical professional check the site of the injected PPD for a reaction. At that later time, the injection site is observed for the presence and amount (diameter) of swelling or induration. A lack of induration typically means a negative result, however false negative results may be obtained in patients with compromised immune function even though the patient is not free of TB. Other factors such as steroid therapy, poor nutrition, compromised immune systems and viral infection can also lead to false negative PPD results. The prolonged period required to obtain a result using the Mantoux test is not at all efficacious. Accordingly, it is a pervasive desire in the field to reduce the amount of time to obtain a reliable test (screening) result.

Another diagnostic test for determining whether a patient has a latent TB infection is the QuantiFERON® Gold bold test. This ELISA-based diagnostic test is a type of interferon-gamma release assay in which a blood sample must be drawn from a patient and deposited into tubes containing peptides from three TB antigens (i.e., ESAT-6, CFP-10, and TB7.7). Exposure of viable lymphocytes in the blood sample to the highly specific TB antigens causes the lymphocytes to produce Interferon y, which is then measured. If Interferon y is present in an amount exceeding a predetermined value, the sample is then deemed to be positive for TB.

Figure 5A:
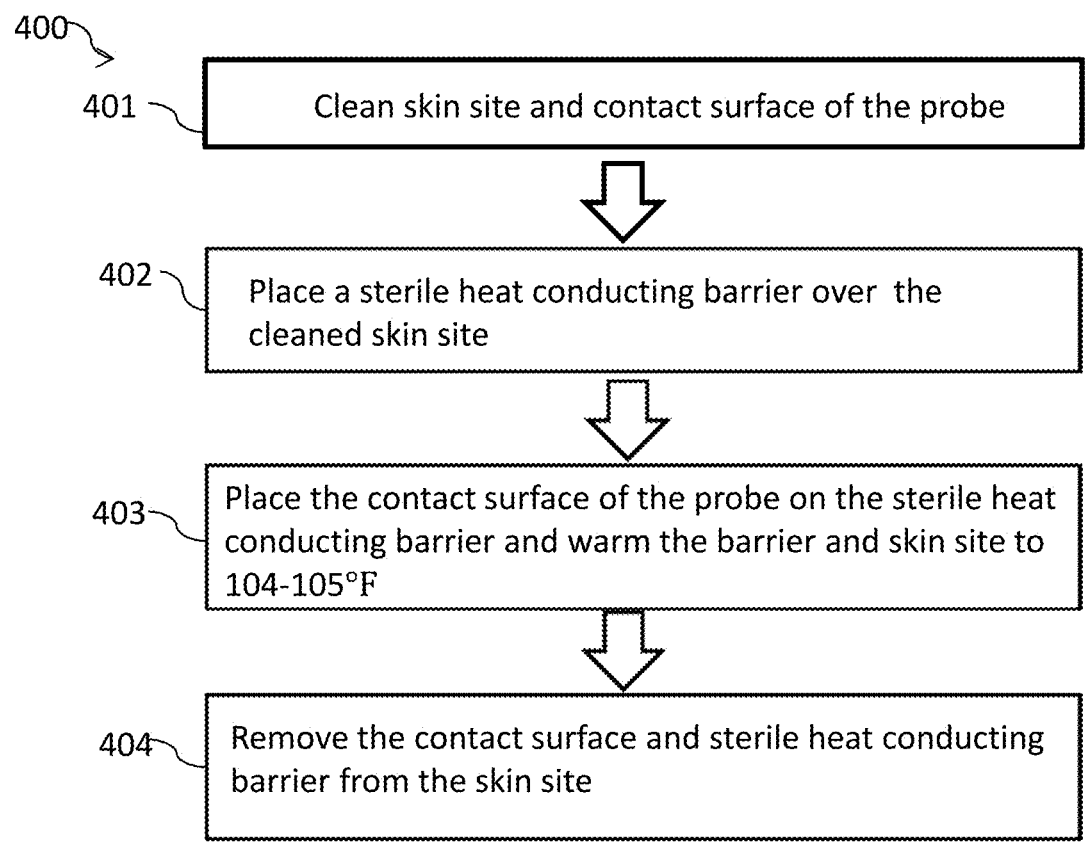
FIG. 5(a) illustrates a flow chart describing a first part of a method for inducing and evaluating an immunological response to an antigen administered epicutaneously in accordance with aspects of the invention.
Figure 5B:
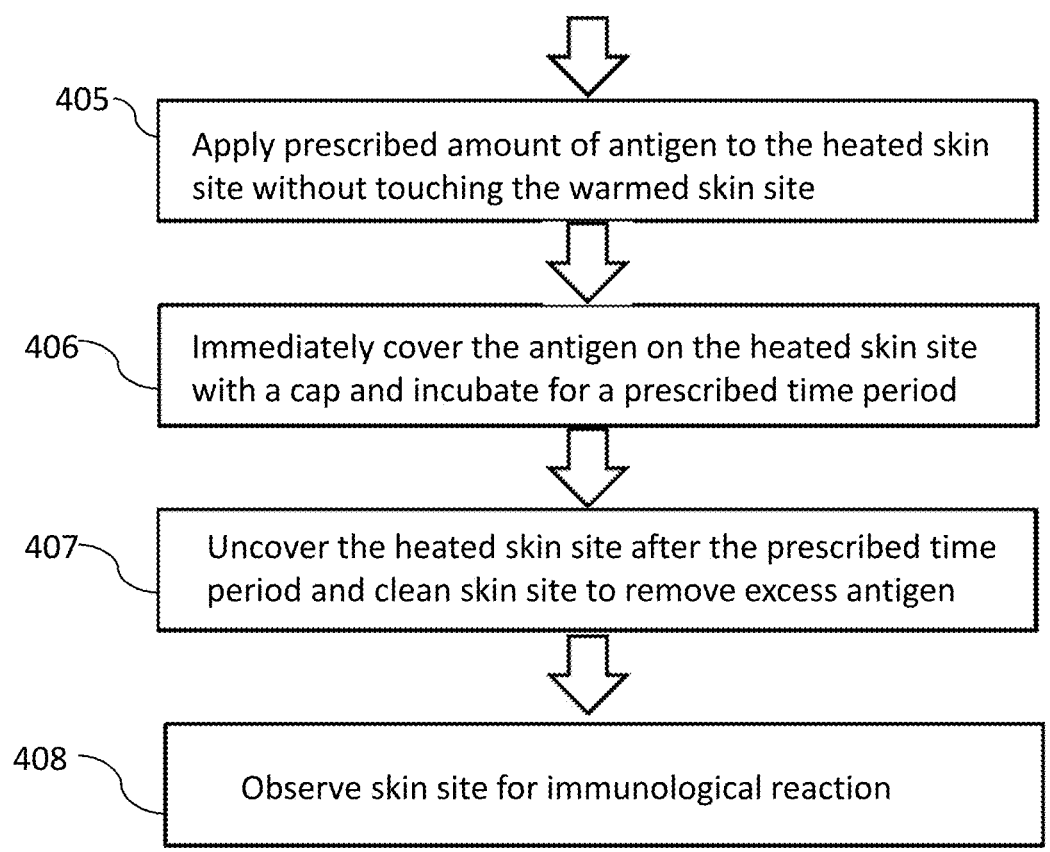
FIG. 5(b) illustrates a flow chart describing a second part of the method of FIG. 5(a)

Referring to FIGS. 5(a) and 5(b), administration of a immunological test, and more specifically a purified protein derivative (PPD) tuberculin test, is described in accordance with a novel thermal epicutaneous induction (TEI) method 400 per an embodiment of the present invention. The TEI method 400, which is schematically illustrated in the flowcharts presented in FIGS. 5(a)-5(b), differs considerably from the standard Mantoux test in that the inventive method is performed epicutaneously using, for example, the skin heating device 10, 200 previously described to administer a predetermined amount of heat to a skin site(s) prior to application of the antigen. For purposes of this discussion that follows, the method 400 is performed at a single skin site of the patient using the skin surface (tissue) heating device 10.

The steps of the inventive method 400 now follow with reference to FIGS. 5(a) and 5(b). Referring to step 401, an area of the patient's skin surface, such as the forearm, is first sterilized with an alcohol wipe or any other suitable means that is typically used to sterilize an area of skin in a medical setting. In advance of step 401, the professional or the patient may optionally add a topical cream containing a moisturizing agent directly to the skin surface area. With reference to FIGS. 1(a) and 1(b), the contact surface 54, 153 of the probe 50 or skin contact portion 150 of the skin heating device 10, 100 is also sterilized. At step 402, a sterile barrier is applied to the sterilized surface of the patient's skin. In an embodiment, this barrier may be a piece of aluminum foil or any other thermally conductive material used to separate or isolate the contact surface 54, 153 of the probe 50 or skin contact portion 150 from the sterilized skin surface. Alternatively, the preceding step 402 may be omitted and the contact surface 54 of the probe 50 may be placed directly onto the sterilized skin surface.

The contact surface 54, 153 of the probe 50 or skin contact portion 150 is placed onto the sterile barrier according to step 403 and heated using the contained heating source of the device 10, 100 to a temperature in the range between about 103-105° F. or preferably to about 104° F. It has been found that heating the skin surface of the patient to a temperature between 103-105° F. improves the permeability of the skin, making the skin better able to absorb the antigen. In at least one version, the heating source of the probe 50 or the skin contact portion 150 may be energized in advance of placement on the sterilized skin surface depending on the temperature of the treatment room or medical facility to expedite the test procedure. The contact surface 54, 153 and sterile barrier are then removed according to step 404. In an embodiment, once the skin surface reaches 103-105° F., it may be maintained at this temperature range for 1-3 minutes before the contact surface 54, 153 and sterile barrier are removed. Application of heat to the skin surface for a prolonged period of time may inhibit a fast cooling of the skin surface prior to and/or during application of the antigen.

Referring to step 405 of FIG. 5*b*, a prescribed amount of antigen, in this case a prescribed amount of PPD tuberculin in solution, is applied onto the heated skin site using a syringe. Because the antigen is often stored in cooled environments such as a refrigerator, the antigen may be held in the hands of the patient, or otherwise, in order to pre-warm the antigen closer to the temperature of the skin site prior to application.

Following step 405, the heated skin site with the applied antigen is then covered with a cap at step 406 and incubated for a predetermined period of time. As referred to herein, the "cap" used for incubation may be a rigid structure sized and configured to contact the heated skin surface around its perimeter in order to surround and effectively contain the deposited antigen, such that the antigen remains in contact with the skin and does not spread beyond the locally heated skin site. In an embodiment, the cap may have a hollow cylindrical shape with an open end that contacts the skin surface and surrounds the deposited antigen. An opposing closed end of the cap may act to further contain the deposited antigen on the skin surface. It will be understood that the function of the cap can be suitably achieved by a variety of shapes and configurations in addition to the version described herein. In addition to the cap, a flexible bandage or similar wrapping can also be placed over the heated skin site in order to maintain the heat of the skin site area as long as possible. Alternatively, an incandescent lamp or other heat source can also be directed toward the heated skin site. During the TEI treatment method 400 discussed herein, it is preferred that the heated skin surface remains incubated. Accordingly, it is preferred that air conditioning and/or fans capable of moving air and affecting ambient temperature in the caregiver's office or treatment room are turned off. Movement of air could prematurely reduce or hasten reduction of the temperature of the heated skin site and is discouraged.

In this specific embodiment, the PPD tuberculin antigen solution is incubated on the heated skin site for up to about 5 minutes. However, it will be realized that the incubation time may be longer or shorter depending upon the antigen(s) used. In any event, it will be readily understood that the incubation period required to perceive a test result is considerably shorter (a matter of minutes) than the 48-72 hours required for the standard Mantoux test. After the desired incubation time has elapsed, the cap and the applied antigen are removed from the heated skin site in step 407. Removal of the antigen from the heated skin site may require additional cleaning of the skin with an alcohol wipe, hot water and soap, or any other accepted method used to clean the surface of the skin. The heated skin site is then observed (step 408) over a predetermined period of time for an immunologic reaction such as redness, swelling, or any other visually perceptible indicator.

The administration of the antigen may alternatively be done using the hydrogel layer 176 of the skin contact portion 170 of the embodiment previously described in FIG. 3(*g*). In this embodiment, the hydrogel layer or coating 176 is impregnated with a dosage of antigen. The heating matrix 174 heats the hydrogel layer 176, which is in contact with the heated skin site. The hydrogel layer 176 is thermally activated, such that heating the hydrogel layer 176 causes the release of the antigen dose onto the heated skin surface.

In another embodiment, an antigen cap 650 is used to administer a dosage of antigen to the heated skin surface. Referring to FIGS. 8(*a*)-(*d*), the antigen cap 650 according to this embodiment generally comprises a base or bottom portion 652, and a top portion 662.

The base portion 652 includes one or more sides 654 that define an interior space 659 and a perimeter having a contact end 651. The interior space 659 is open proximate the contact end 651. The base portion 652 further comprises a holder 656 configured to retain an antigen dosage or antigen capsule A. One or more piercing elements 657 are positioned within the holder 656. The top portion 662 is movably coupled to the base portion 652 such that the top portion 662 can move between an open position in which the holder 656 is accessible, and a closed position in which the top portion 662 inhibits access to the holder 656 and is otherwise covered by the top portion 662. As shown, the moveable coupling of the top portion 662 to the base portion 652 may be accomplished using a hinge 660; however, in other embodiments the top and bottom portions 652, 662 may be enabled to slide relative to each other between respective open and closed positions. The top portion 662 includes one or more sides 664 defining a perimeter. The top portion 662 further includes a top surface 661 and an opposing bottom surface 663. A compression member 666 is positioned or formed on the bottom surface 663. When the antigen cap 650 is in the closed position, the compression member 666 extends from the bottom surface 663 of the top portion 662 towards the holder 656 and exerts a force on the antigen capsule A towards the one or more piercing elements 657. The top portion 662 may further include one or more piercing elements 667 that extend from the compression member 666. As shown, each of the piercing elements 657, 667 are spikes. The antigen cap 650 may be formed from a variety of medical grade, non-reactive materials, such as plastic and stainless steel. In an embodiment, one or more parts of the antigen cap 650 may be transparent, opaque or otherwise colored, or a combination of both.

In order to administer antigen using the antigen cap 650, the antigen cap 650 is placed over the heated skin surface such that the contact end 651 of the base portion 652 contacts the heated skin portion. An antigen capsule A is placed in the holder 656 and the top portion 662 is moved into the closed position in which the compression member 666 engages the antigen capsule A and presses the capsule into the one or more piercing elements 657 of the holder 656. This acts to pierce and crush the antigen capsule A to release the dose of antigen into the interior space 659, through the open end proximate the contact end 651, and onto the heated skin surface. The antigen cap 650 is left in place and in the closed position after release of the antigen dosage for the prescribed amount of time before being removed and the heated skin surface is cleaned of excess antigen.

As described herein, the "heated skin site" refers to the portion of the surface of the skin that was heated by the contact surface 54, 153 and then was in contact with the antigen. Over time, the heated skin site will revert to its normal surface temperature. However and for the purposes of this discussion, this area will continue to be referred to as the heated skin site, even after the incubation period has elapsed. In the case of the herein described PPD tuberculin test, the observation time may be between 1-4 hours, however, it will be understood that observation times for different antigens may vary from this range. In an embodiment and to avoid having to remain in the physician's office, the patient may be able to take a picture or video of the heated skin site at a predetermined observation time. For example, the patient can utilize the camera of a smart device, such as a smart phone or tablet computer, and subsequently email the picture(s)/video to a physician or other medical professional for evaluation.

Figure 8A:
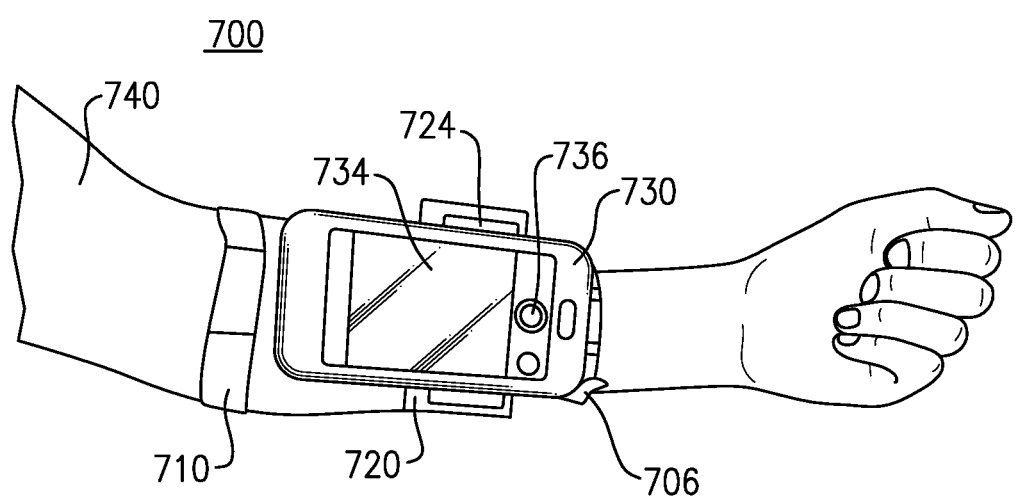
FIG. 8(a) illustrates a top view of a supporting apparatus in accordance with an embodiment, the supporting apparatus configured to capture images from a patient following an allergen-specific epicutaneous immunotherapy treatment in accordance with aspects of the invention.
Figure 8B:
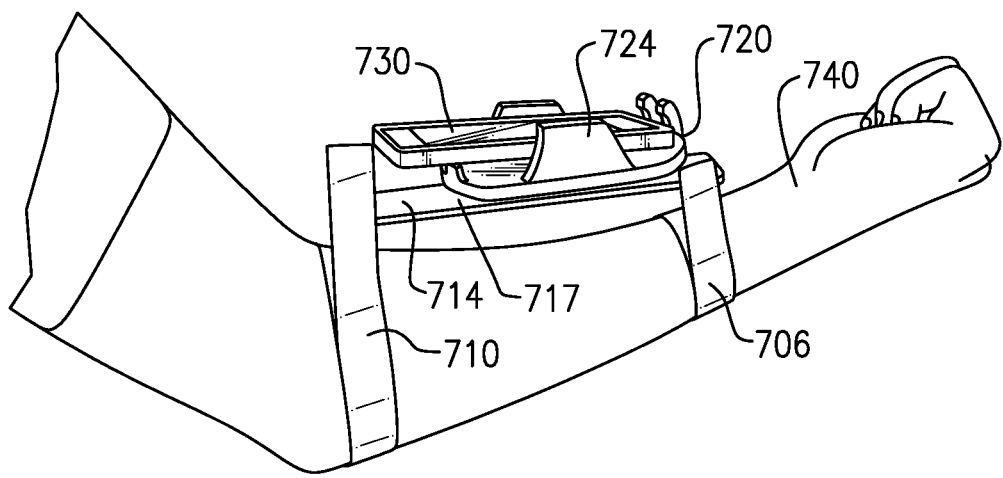
FIG. 8(b) illustrates a side view of the supporting apparatus of FIG. 8(a)

An example of a supporting apparatus 700 used in conjunction with a smart device is configured to capture pictures and videos of a skin site heated in accordance with the method 400 for storage and transfer is illustrated in FIGS. 8(a) and 8(b). This supporting apparatus 700 includes a pair of straps 706, 710 provided on opposing sides of the apparatus 700 that are sized and configured to be wrapped about the forearm of a patient 740. In one version, the straps 706, 710 include hook and loop fasteners to permit attachment. In another version, the straps 706, 710 can be made from an elastic material formed as loops that can be secured over the forearm of the patient 740.

Each of the straps 706, 710 according to this embodiment are disposed at opposing ends of a lower planar support 714, the latter preferably including a through aperture 717 formed at one end, adjacent the elastic strap 710. Preferably, the lower support 714 is made from an optically transparent material, such as Plexiglas®. A smart device supporting member 720 is fixedly attached to the top or upper surface of the lower support 714. The supporting member 720 is defined by a body having a pair of inwardly directed clamping members 724 on opposing lateral sides of the upper facing side of the supporting member 720. The clamping members 724 are preferably made from a resilient and flexible plastic and are spaced relative to one another to permit a smart device 730, such as a smart phone, to be releasably attached.

In terms of operation and following the incubation period, the elastic straps 706, 710 are used to secure the apparatus 700 to the forearm of the patient 740 with the camera of the smart device 730 being aligned over the heated skin site. When attached, the camera is aligned with the formed aperture 717 of the lower support 714. The heated skin site can be viewed via the outwardly facing display 734 of the attached smart device 730. The camera of the supported smart device 730 can be accessed by the user in order to capture images over time using, for example, the image or video capture button 736. In one version, the smart device 730 can be configured or programmed with a timer function that captures a predetermined number of images or videos according to a predetermined schedule. The captured images can be automatically stored to the memory of the smart device 730 and e-mailed to the cloud or directly to a medical facility for purposes of records and evaluation.

Figure 9:
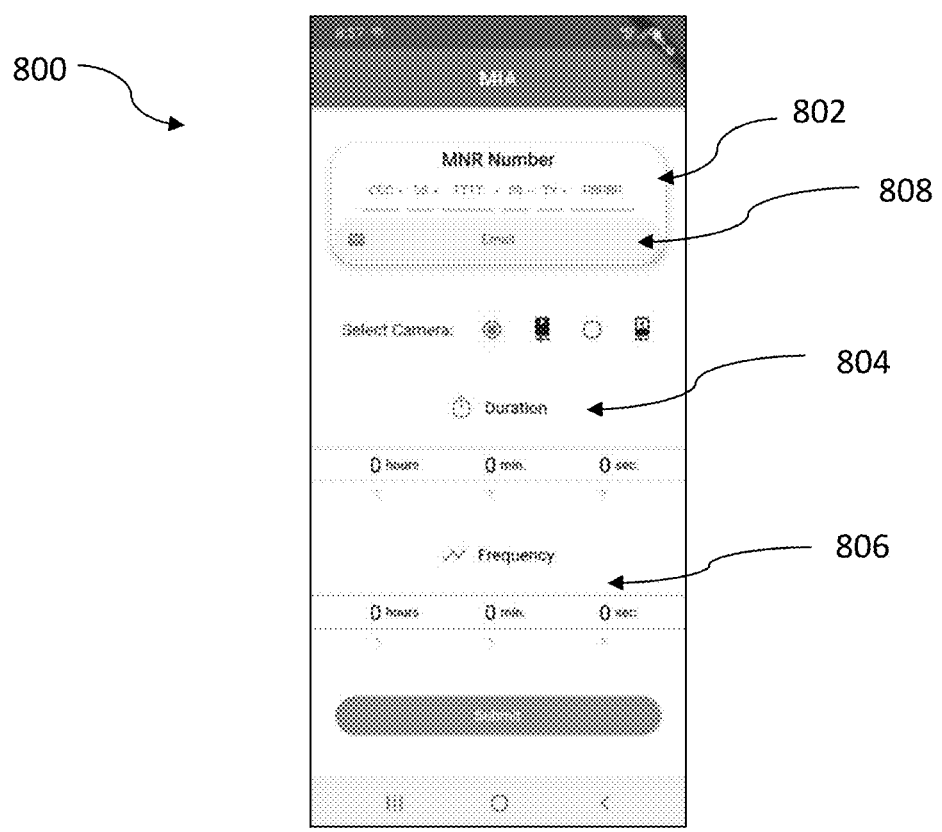
FIG. 9 illustrates an embodiment of a user interface of an application to assist in image capture and transmission.

The smart device 730 may have an uploaded application that is able to accesses the camera of the smart device 730 (FIGS. 8(a)-(b)). Referring to the example of the application interface 800 displayed on the smart device 730 (FIGS. 8(a)-(b)) shown in FIG. 9, the application interface 800 can allow a user and/or the medical professional to set up a profile for the patient user. In an example, the medical professional may be able to set up an initial user patient profile to include medical identification, such as a file number 802, codes as well as preprogrammed protocol with a specific time period or duration of time 804 during which images of the heated skin site will be captured and a predetermined frequency 806 of image capture during the period of time. The user/patient may be able to securely log into the application and edit the patient/user profile to include contact information 808, such as email and mailing addresses. In an embodiment, the patient/user may also be able to access and change the duration of time 804 and frequency 806. Once the parameters of the application are set by the medical professional and/or the user/patient, the application accesses the camera of the smart device 730 (FIGS. 8(a)-(b)). The application controls the camera to obtain images of the heated skin area according to the entered protocol. The images may be stored in memory on the smart device 730 (FIGS. 8(a)-(b)) for later submission to the medical professional or may be stored and automatically sent to the medical professional as the images are obtained. The application interface used by the medical professional may allow access to the images, the ability to sync the user profile with a specific medical record, and/or the ability to communicate with the patient/user. Once the images are accessed and evaluated by the medical professional, the medical professional may communicate the results to the patient/user through the application.

The herein described TEI method 400 eliminates the need for intradermal application of the antigen, in this case the PPD tuberculin. Moreover, the herein described TEI method 400 enables an immunological response to be obtained much faster than the standard Mantoux test. Reliable test results can be obtained for evaluation in a matter of hours, rather than days. Allowing for photo submissions of the heated skin site also eliminates the need for a follow-up visit to the physician's office for evaluation. In addition, the herein described TEI method 400 has been shown to be equally effective in both child and adult patients of varying ages.

As noted, the herein described TEI method 400 can be performed on a single skin site using the heating device 10, FIGS. 1(*a*)(*b*), or upon multiple adjacent skin sites of a patient simultaneously using the heating device 200, FIG. 3(*c*).

TEI Immunization Method

The principles of the herein described thermal epicutaneous therapy method 400 can be adapted to a number of different and varied applications and uses. For example and as described in this section, the previously described TEI method can also be used for the purpose of administering a booster or secondary immunization. In accordance with one specific example, Pentacel is a vaccine used to improve immunity against diphtheria, haemophilus influenzae type B, pertussis, polio, and tetanus, each of which are serious diseases that are caused by bacteria or viruses. For patients who have already been immunized by a conventional intramuscular injection of Pentacel, Applicant has determined that a booster may be administered as a secondary immunization using a TEI immunization method. An exemplary version of this method 500 is herein described with reference to FIGS. 6(*a*) and 6(*b*), using the skin surface (tissue) heating device 10 for testing at a single skin site. Alternatively, the method can also be conducted using the heating device 200 at a plurality of adjacent skin sites.

Additional methods will be described with reference to one embodiment of the skin heating device 10, however it should be obvious to one skilled in the art that any of the embodiments described herein may be used. Step 501 of the thermal epicutaneous immunization method 500 comprises cleaning the skin surface, as well as the contact surface 54, (FIGS. 1(*a*) and 3(*b*)) of the probe 50 of the skin heating device 10 using a suitable cleaning agent. In addition and prior to cleaning the skin surface, the patient or professional may also preferably apply a cream or other topical treatment having a moisturizing agent to the skin site. As discussed previously, it has been determined that application of a moisturizing agent in advance of treatment better prepares the skin for immunotherapy. At step 502, a sterile barrier is placed over the cleaned skin site. The sterile barrier according to at least one version can be a suitably sized section of aluminum foil or any other thermally conductive material used to separate or isolate the contact surface 54 of the probe 50 from the sterilized skin surface. Alternatively, the preceding step 502 may be omitted and the contact surface 54 of the probe 50 may be placed directly onto the sterilized skin surface. The contact surface 54 (FIGS. 1(*a*) and 3(*b*)) of the probe 50 of the skin surface heating device 10 is then placed onto the sterile barrier in step 503 and the contact surface 54 is heated to a predetermined temperature of about 103-105° F., and more preferably to about 104° F. The device 10 (or 200) is configured to automatically deenergize the heating source once the predetermined temperature has been reached, as sensed by the temperature sensor. According to at least one version, the skin surface heating device 10 or 200 may further include an indicator that is configured to produce a visual or audible signal to the user when the predetermined temperature has been reached. Once the predetermined temperature has been reached, the contact surface 54 (FIGS. 1(*a*) and 3(*b*)) and the sterile barrier are then removed according to step 504.

Figure 6A:
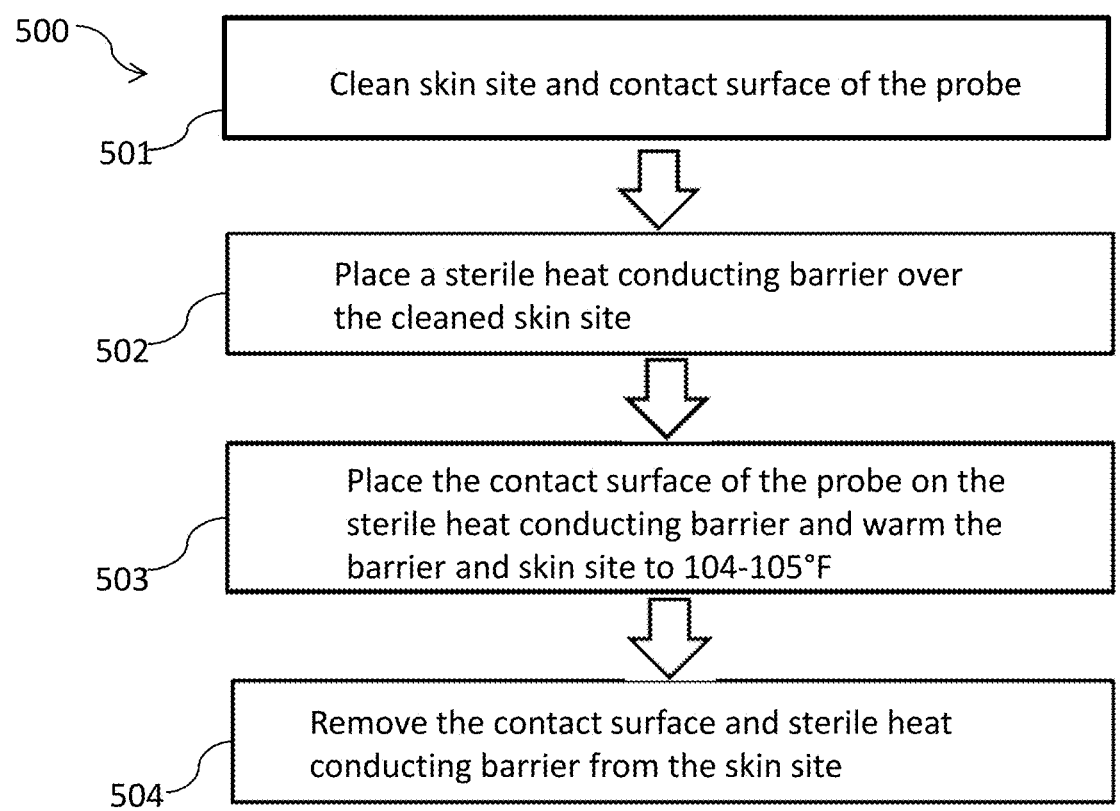
FIG. 6(a) illustrates a flow chart describing a first part of a method for administering a secondary immunization epicutaneously in accordance with aspects of the invention.
Figure 6B:
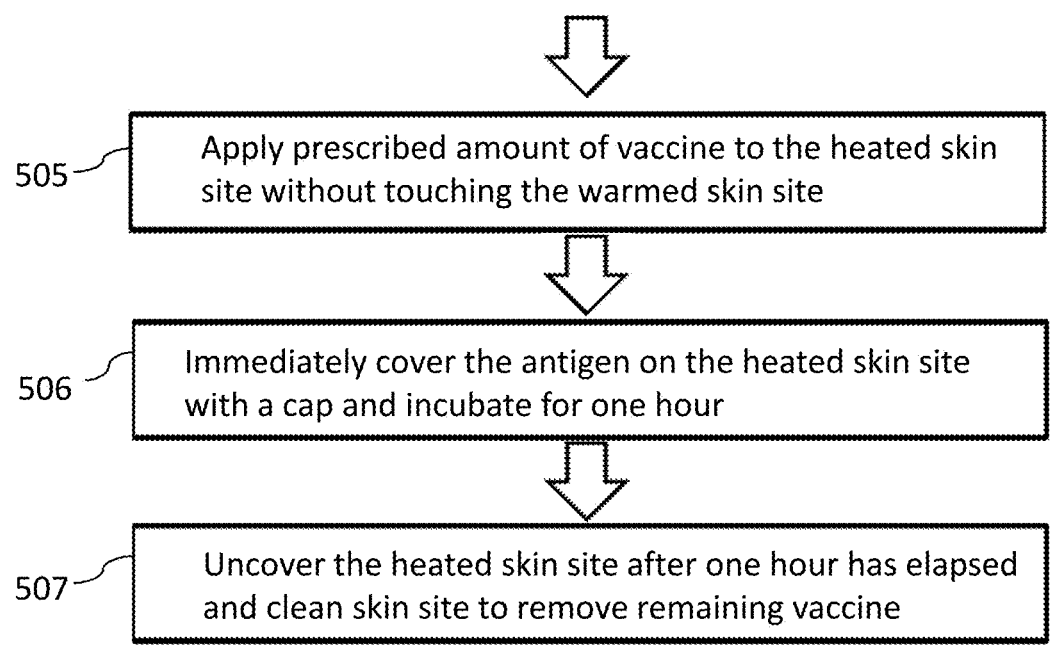
FIG. 6(b) illustrates a flow chart describing a second part of the method of FIG. 6(a)
Figure 7A:
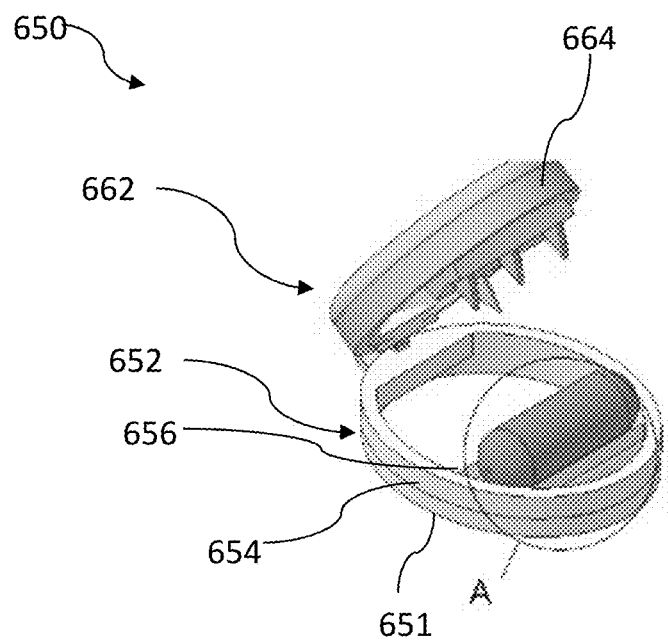
FIG. 7(a) illustrates a side perspective view of an embodiment of an antigen cap for administering a dose of antigen.
Figure 7B:
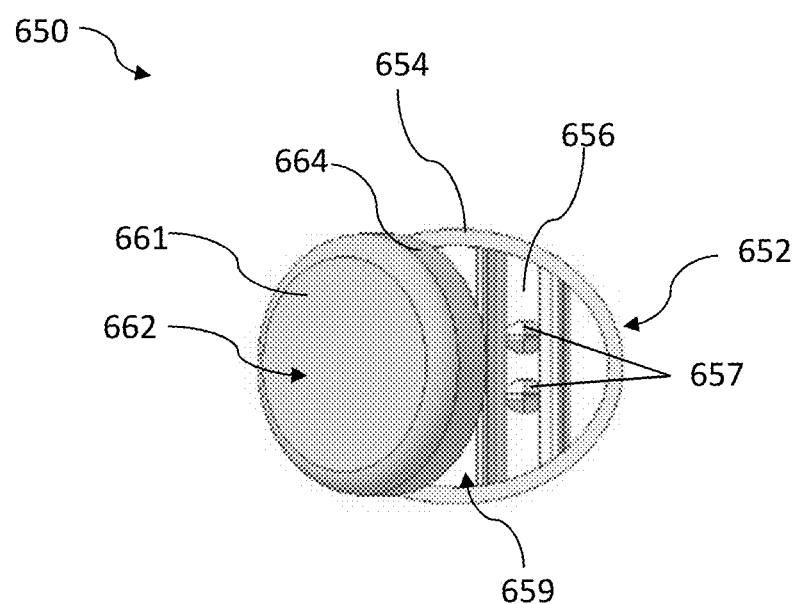
FIG. 7(b) illustrates a top perspective view of the antigen cap of FIG. 7(a)
Figure 7C:
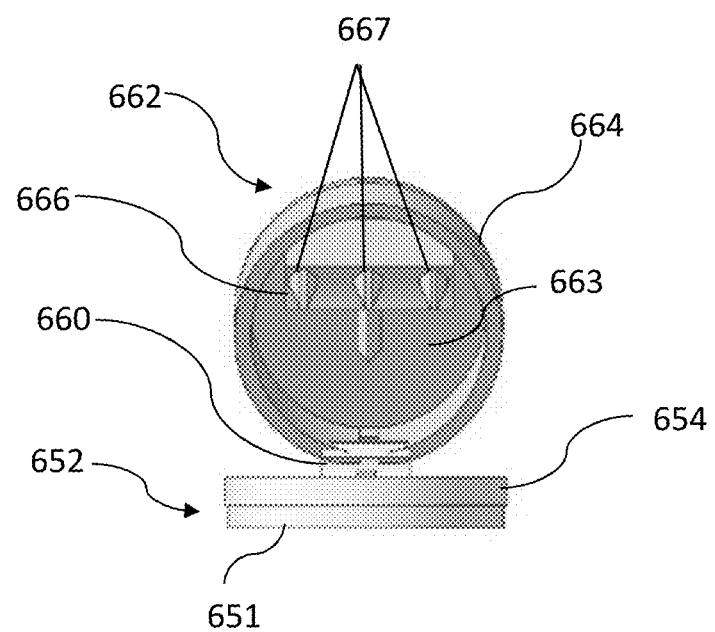
FIG. 7(c) illustrates a front view of the antigen cap of FIG. 7(a)
Figure 7D:
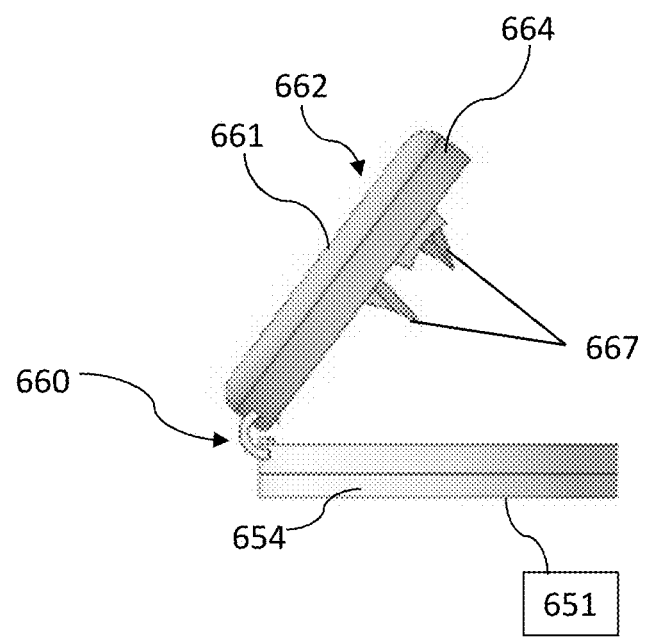
FIG. 7(d) illustrates a side elevational view of the antigen cap of FIG. 7(a)

Referring to step 505 of FIG. 6(*b*) and according to this specific method, a prescribed amount of vaccine (i.e., Pentacel) is applied directly onto the heated skin site. In this example, 0.1 mL of Pentacel is dispensed onto the heated skin surface, which is considerably less than the 0.5 mL used in a standard intramuscular injection of Pentacel. When dispensing the Pentacel, it is important not to contact the heated skin site with the dispenser (e.g. pipette, syringe, etc. . . . ), finger, or anything that may cause contamination or otherwise corrupt the end results of the herein described TEI method 500. In addition and depending on where the antigen is stored initially, it may be preferred for the patient or the professional to pre-warm the antigen in the dispenser prior to application of same.

The heated skin site with the applied vaccine is then covered with a cap at step 506 and incubated for a predetermined period of time. As referred to herein, the "cap" used for incubation may be a rigid structure sized and configured to contact the heated skin surface around its perimeter in order to surround and effectively contain the deposited antigen, such that the antigen remains in contact with the skin and does not spread beyond the locally heated skin site. In an embodiment, the cap may have a hollow cylindrical shape with an open end that contacts the skin surface and surrounds the deposited antigen. An opposing closed end of the cap may act to further contain the deposited antigen on the skin surface. It will be understood that the function of the cap can be suitably achieved by a variety of shapes and configurations in addition to the version described herein such as those previously described and shown in FIGS. 8(*a*)-8(*d*). The cap can also be shaped to cover more than one heated skin sites in the event adjacent skin sites are selected. In addition to the cap, a flexible bandage or similar wrapping can also be placed over the cap and the heated skin site in order to maintain the heat of the skin site area as long as possible. Alternatively or in combination, the heated skin site can be exposed to an incandescent or other lamp during incubation. In this specific example involving Pentacel, the incubation period is approximately 1 hour. It will be noted, however, that the incubation period may be longer or shorter depending upon the vaccine.

After the incubation time has elapsed, the cap and remaining vaccine are removed from the heated skin site in step 507. Removal of the antigen from the heated skin site may require additional cleaning of the skin with an alcohol wipe, hot water and soap, or any other accepted method used to clean the surface of the skin. The heated skin site may then observed over a predetermined period of time for an immunologic reaction such as redness, swelling, or any other visual sign. The heated skin site refers to the portion of the surface of the skin that was initially heated by the contact surface 54 and then was in contact with the deposited vaccine or antigen. Over time, this heated skin site will revert to its normal surface temperature, however for the purposes of this discussion the skin site will still be referred to as the heated skin site.

Sequential Epicutaneous Immunotherapy

Figure 10:
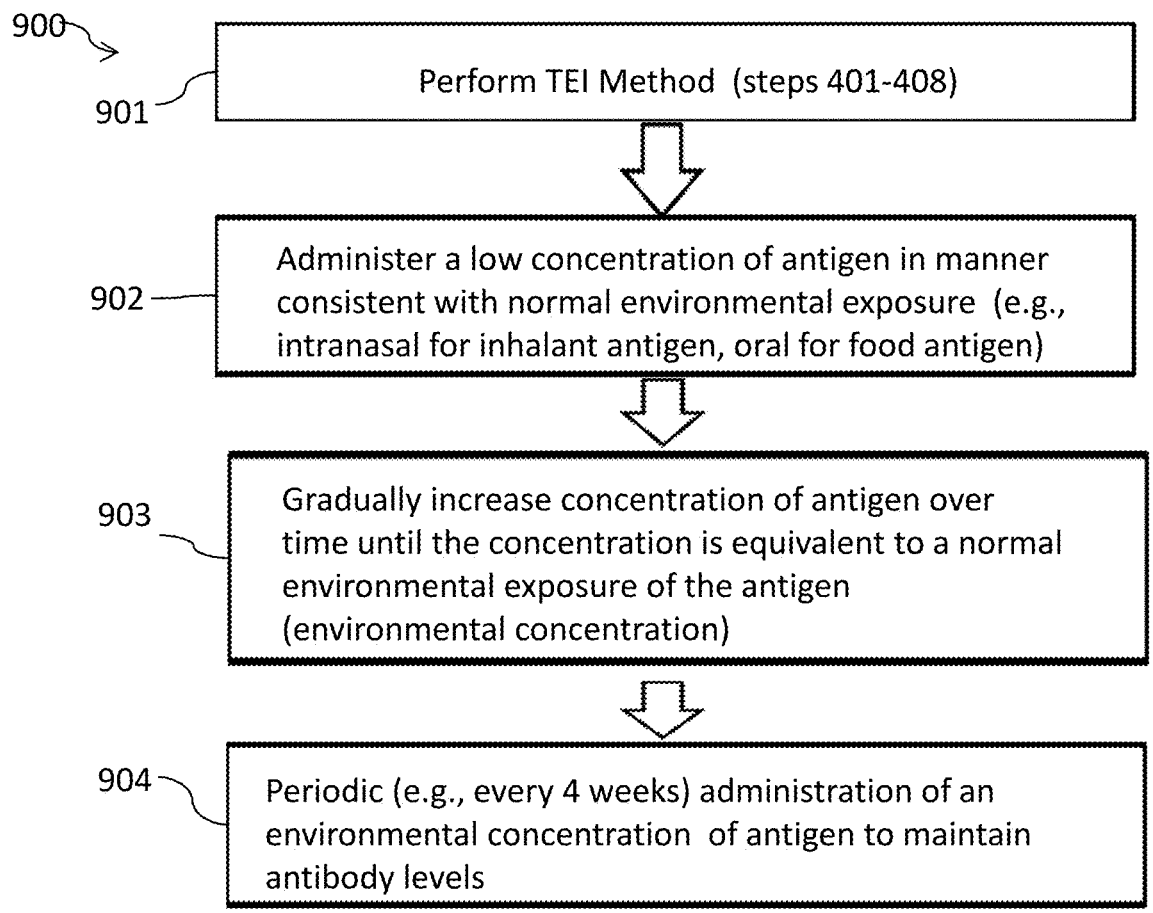
FIG. 10 illustrates a flow chart describing a method for allergen-specific epicutaneous immunotherapy in accordance with aspects of the invention.

The above described TEI method 400 of inducing an immunological response may be used by itself as previously described with reference to FIGS. 5(*a*)-5(*b*) or incorporated as part of a sequential epicutaneous immunotherapy (SEIT) that is designed to evaluate and desensitize a patient to a specific antigen. A method is herein described with reference to FIG. 10 in which an exemplary SEIT methodology 900 may commence according to the previously disclosed TEI method 400, step 901, in order to first induce an immunological response from a patient to an antigen through epicutaneous exposure to the antigen. Each of the previously discussed steps of the method 400 are performed, including the subcutaneous application of an amount of a specific antigen to a heated skin site(s). In addition to the steps 401-408 as part of step 901, a small amount of an adjuvant can also be added to the skin site prior to the application of the antigen in order to improve the antigenicity of the skin cells.

The heated skin site is observed for redness, swelling, or any other physical change following administration of the antigen and incubation. In accordance with this methodology and based on patient response, the TEI method 400 may be performed a single time (for determining the presence of a disease such as TB) or more preferably for several treatments taken over a defined time period (for vaccination or desensitization). The starting concentration of the antigen is determined by the End Point Titration method. This concentration is the least amount of antigen that elicits a positive response. Each time the TEI method 400 is performed on a subject/patient, the physical effects observed at the heated skin site will decrease in severity and duration based on the immune response of the patient. In addition to the observance of physical changes, blood levels can further be obtained periodically and contemporaneously to evaluate the patient's immunological response to the particular antigen and the production of antibodies against the particular antigen. The results look for tended decrease in specific-IgE antibodies and/or an increase in specific-IgG/specific-IgE antibody ratio.

Following treatment(s) in accordance with the TEI method 400 and according to the herein described SEIT method, step 902, a low concentration of antigen as determined by the End Point Titration method is then administered to the patient in a manner consistent with the patient's normal environmental exposure of the antigen that would ordinarily trigger an allergic response. For example, if the antigen is pollen, then a low concentration of pollen antigen would be nasally administered to the patient. In another example, and if the antigen is present in peanuts, a low concentration of peanut powder/peanut butter would be orally administered. Importantly for this part of the SEIT method, the antigen is administered to the patient in accordance with the usual mechanism that the specific allergen would be introduced to a patient. The usual mechanism is the typical mode of exposure to the allergen in nature. The concentration of the antigen administered is gradually increased over time until the concentration is equivalent to a normal environmental exposure of the antigen (environmental concentration).

Per step 903, it has been determined that the foregoing steps act to increase specific-IgG and specific-IgG4 antibody production, as increased concentrations of antigen are administered on a periodic basis. Accordingly, step 903 may occur over the course of weeks, months, or even years, creating a accumulating tolerance (desensitizing) for the antigen.

After the patient is able to tolerate exposure to the antigen at an environmental concentration, regular maintenance of the patient's antibody concentration is required per step 904. For example, in the case of the antigen being present in peanuts, oral ingestion of a small amount of peanuts once or twice per week may be required for maintenance. In the case of a dust mite allergy, a person's normal routine typically exposes them to sufficient amounts of dust such that additional maintenance measures may not be required. SEIT can be used, as discussed, in combination with other immunotherapy methods.

With reference to the treatment with regard to peanut allergy, the initial epicutaneous treatment helps to inhibit or lessen any anaphylactic reaction due to the subsequent peanut exposure. The epicutaneous treatment may act to stimulate the production of T-cells and specifically the production of T-cells in a ratio where T-helper2 (Th2) cells<T-helper 1 (Th1) cells. The Th2 cells are primarily responsible for the adverse inflammatory reactions and Th1 cells down-modulate the effects of the Th2 cells. The subsequent oral therapy (as opposed to a nasal treatment) also promotes the production of Th1 cells. The increased number of Th1 cells inhibits or decreases the frequency of adverse effects.

With reference to the treatment with regard to pollen allergy, the initial epicutaneous treatment inhibits negative reactions such as Eosinophilic Esophagitis, which may occur if stepped oral pollen doses are given without the initial epicutaneous treatment. Similar immunological effects are experienced as with peanuts as discussed above.

The system and methods described herein may also be at least partially applicable for desensitizing patients to a variety of allergens not specifically mentioned such as ragweed and grass, among others. As discussed, desensitization can be done without injections or transdermal patches and is effective in adults, as well as children. Since the methods described are epicutaneous, the antigen has no access to the blood stream such that there is a very low risk of a systemic reaction to the treatment.

In addition to the applications described, it should be noted that the herein described methods may further be used to determine the presence of various autoimmune diseases, presence of other infectious diseases, certain types of cancer, or various other diseases that typically require blood tests and/or radiologic imaging for purposes of diagnosis.

PARTS LIST FOR FIGS. 1a-8(b)

10 skin surface (tissue) heating device
20 housing
24 controller
30 electrical connection, power source and probe
50 probe
52 body, probe
54 probe contact surface
56 temperature sensor
58 display
60 controller (timer)
200 skin surface (tissue) heating device
204 housing
205 horizontal base, housing
207 flexible enclosure
208 heating elements
210 support
212 body, heating elements
215 slots, horizontal base
216 heating surfaces
220 temperature sensor
225 input terminal, heating element
227 output terminal, heating element
229 insulating washer
231 header
233 thermostat relay
235 wire
237 electrical line
239 electrical line
241 insulating piece
250 power supply 400 method
401 step
402 step
403 step
404 step
405 step
406 step
407 step
408 step
500 method
501 step
502 step
503 step
504 step
505 step
506 step
507 step
650 antigen cap
651 contact end, antigen cap
652 top portion, antigen cap
654 one or more sides, bottom portion
656 holder, bottom portion
657 one or more piercing elements, bottom portion
659 interior space, bottom portion
660 hinge, antigen cap
661 top surface, top portion
662 bottom portion, antigen cap
663 bottom surface, top portion
664 one or more sides, top portion
666 compression member, top portion
667 one or more piercing elements, top portion
700 supporting apparatus
706 elastic strap
710 elastic strap
714 lower support
717 aperture, lower support
720 smart device supporting member
724 clamping members
730 smart device
734 display
736 image or video capture button
740 patient
800 interface, application
802 file number, interface
804 duration of time, interface
806 frequency, interface
808 contact information, interface
900 method
901 step
902 step
903 step
904 step Additional embodiments include any one of the embodiments described above and described in any and all exhibits and other materials submitted herewith, where one or more of its components, functionalities or structures is interchanged with, replaced by or augmented by one or more of the components, functionalities or structures of a different embodiment described above.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

The invention claimed is:

1. A method of immunological evaluation, the method comprising:
   i) cleaning a skin surface area of a patient;
   ii) applying a controlled and uninterrupted amount of heat to the skin surface area until a predetermined temperature has been reached;
   iii) removing the controlled and uninterrupted amount of heat after the skin surface area reaches the predetermined temperature;
   iv) administering an amount of an antigen to the skin surface area;
   v) incubating the antigen for a predetermined amount of time on the skin surface area;
   vi) removing the antigen from the skin surface area; and
   vii) evaluating an immunological response at the skin surface area,
   wherein the skin surface area remains intact throughout each of the above steps.

2. The method of claim 1, further comprising subsequently administering a dose concentration of the antigen in an escalating manner over a predetermined period of time consistent with subcutaneous immunotherapy exposure to the antigen, wherein the dose concentration of the antigen is gradually increased over the predetermined period of time but remains less than a concentration of the antigen at a normal environmental exposure.

3. The method of claim 2, further comprising stimulating production of T-helper 1 cells and T-helper 2 cells, wherein the T-helper 1 cells are produced in greater number than the T-helper 2 cells and down-modulate the inflammatory effects triggered by the dose concentration of the antigen.

4. The method of claim 3, further comprising administering a dose concentration after expiration of the predetermined period of time, wherein the dose concentration is a concentration of the antigen that is equivalent to the normal environmental exposure of the antigen, and wherein the dose concentration is administered in a manner consistent with normal environmental exposure.

5. The method according to claim 1, wherein the predetermined temperature is from about 103° F. to about 105° F.

6. The method of claim 1, wherein the predetermined amount of time for incubating antigen is from about one (1) to about four (4) hours.

7. The method of claim 1, further comprising covering the skin surface area during the incubation of the antigen on the skin surface area.

8. The method of claim 1, wherein the administering of the amount of the antigen to the skin surface area comprises, placing an antigen cap on the skin surface area, placing an antigen capsule containing a predetermined amount of antigen into a base portion of the antigen cap, and closing a top portion of the antigen cap, the top portion comprising one or more spikes configured to pierce the antigen capsule and releasing the predetermined amount of antigen onto the skin surface area during the closing of the top portion.

9. The method of claim 1, wherein the evaluating the immunological response at the skin surface area comprises viewing the skin surface area;

capturing at least one image of the skin surface area; and transmitting the captured images of the skin surface area remotely to a medical professional.

10. The method of claim 9, further comprising positioning a smart device supported at the skin surface and configured to evaluate the immunological response at the skin surface area.

11. The method of claim 4, wherein the normal environmental exposure comprises airborne exposure.

12. The method of claim 4, wherein the normal environmental exposure comprises ingestion.

13. The method of claim 1, further comprising applying a moisturizing agent to the skin surface area prior to the cleaning the skin surface area.

* * * * *